US010717771B2

(12) United States Patent
Simon et al.

(10) Patent No.: US 10,717,771 B2
(45) **Date of Patent: *Jul. 21, 2020**

(54) TREATMENT OF ISCHEMIA

(71) Applicant: MOREHOUSE SCHOOL OF MEDICINE, Atlanta, GA (US)

(72) Inventors: Roger P. Simon, Atlanta, GA (US); Zhi-Gang Xiong, Atlanta, GA (US)

(73) Assignee: MOREHOUSE SCHOOL OF MEDICINE, Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/985,761

(22) Filed: May 22, 2018

(65) Prior Publication Data

US 2018/0273591 A1 Sep. 27, 2018

Related U.S. Application Data

(63) Continuation of application No. 15/167,702, filed on May 27, 2016, now Pat. No. 10,005,822, which is a continuation of application No. 14/660,581, filed on Mar. 17, 2015, now Pat. No. 9,381,227, which is a continuation of application No. 13/284,166, filed on Oct. 28, 2011, now Pat. No. 9,745,356, which is a continuation of application No. 11/724,859, filed on Mar. 16, 2007, now Pat. No. 8,076,450.

(60) Provisional application No. 60/611,241, filed on Sep. 16, 2004.

(51) Int. Cl.

| | |
|---|---|
| *C07K 14/435* | (2006.01) |
| *A61K 38/17* | (2006.01) |
| *A61K 38/16* | (2006.01) |
| *A61K 31/439* | (2006.01) |
| *A61K 31/4418* | (2006.01) |
| *A61K 31/4965* | (2006.01) |
| *A61K 31/498* | (2006.01) |
| *A61K 45/06* | (2006.01) |

(52) U.S. Cl.

CPC ...... *C07K 14/43518* (2013.01); *A61K 31/439* (2013.01); *A61K 31/4418* (2013.01); *A61K 31/498* (2013.01); *A61K 31/4965* (2013.01); *A61K 38/16* (2013.01); *A61K 38/17* (2013.01); *A61K 38/1767* (2013.01); *A61K 45/06* (2013.01)

(58) Field of Classification Search

None

See application file for complete search history.

(56) References Cited

U.S. PATENT DOCUMENTS

| | | | | |
|---|---|---|---|---|
| 7,132,505 | B1 | 11/2006 | Lazdunski et al. | |
| 9,381,227 | B2 | 7/2016 | Simon et al. | |
| 10,005,822 | B2 * | 6/2018 | Simon | A61K 38/17 |
| 2007/0087964 | A1 | 4/2007 | Welsh | |
| 2008/0279965 | A1 | 11/2008 | Simon et al. | |

FOREIGN PATENT DOCUMENTS

| | | |
|---|---|---|
| WO | 2001/085931 | 11/2001 |
| WO | 2006/034035 | 3/2006 |

OTHER PUBLICATIONS

Saez et al., "Molecular dynamics and functional studies define a hot spot of crystal contacts essential for PcTx1 inhibition of acid-sensing ion channel 1a", British Journal of Pharmacology 172: 4985-4995 (2015) (Year: 2015).*

Aarts, M. et al., "Treatment of Ischemic Brain Damage by Perturbing NMDA Receptor—PSD-95 Protein Interactions", Science, Oct. 25, 2002, vol. 298(5594), pp. 846-850.

Xiong, Z.G. et al., "Neuroprotection in Ischemia: Blocking Calcium-Permeable Acid-Sensing Ion Channels", Cell, Sep. 17, 2004, vol. 118(6), pp. 687-698.

Bladin, C.F. et al., "Seizures After Stroke: A Prospective Multicenter Study", Arch Neural., Nov. 2000, vol. 57(11 ), pp. 1617-1622.

Anderson, R.E. et al., "Protection of Focal Cerebral Ischemia by Alkalinization of Systemic pH", Neurosurgery, Nov. 2002, vol. 51 (5), pp. 1256-1265.

Brudno, M. et al., "Automated whole-genome multiple alignment of rat, mouse, and human", Genome Research, 2004, vol. 14(4), pp. 685-692.

File History of U.S. Appl. No. 11/724,859, filed Mar. 16, 2007.

File History of U.S. Appl. No. 13/284,166, filed Oct. 28, 2011.

File History of U.S. Appl. No. 14/660,581, filed Mar. 17, 2015.

File History of U.S. Appl. No. 15/167,702, filed May 27, 2016.

* cited by examiner

*Primary Examiner* — Anand U Desai

(74) *Attorney, Agent, or Firm* — Ping Wang; Morris, Manning & Martin, LLP

(57) ABSTRACT

A system, including methods and compositions, for treatment of ischemia.

7 Claims, 10 Drawing Sheets

Specification includes a Sequence Listing.

CONTROL
pH 6.0
500 pA
2 SEC
OGD
pH 6.0
SCALED/SUPERIMPOSED
pH 6.0

CURRENT AMPLITUDE (pA)
2500
2000
1500
1000
500
0
CONTROL
*P<0.05
OGD
* pH 6.0
(τ = 735 ms)
CON
OGD
(τ = 1848 ms)
500 pA
1 SEC
DECAY TIME CONSTANT (ms)
3000
2000
1000
0
CONTROL
**P<0.01
OGD
**

CONTROL
pH 6.0
ASICI-/-
200 pA
2 SEC
OGD
pH 6.0

RELATIVE LDH RELEASE
0.0
0.1
0.2
0.3
0.4
0.5
pH 7.4, 1.3 Ca2+
pH 7.4, 0.2 Ca2+
pH 6.0, 1.3 Ca2+
pH 6.0, 1.3 Ca2+
pH 6.0, 0.2 Ca2+
**
**
**

RELATIVE LDH RELEASE
NONTRANSFECTED
ASIC1a TRANSFECTED
7.4
6.0
7.4
6.0
6.0+ AMILORIDE
*
*

RELATIVE LDH RELEASE
1.0
0.8
0.6
0.4
0.2
0.0
pH 7.4
pH 6.0
pH 6.0 + AMILORIDE
pH 6.0 + PcTX VENOM
NMDA + GLYCINE
ASIC1+/+
ASIC1-/-
**
**
**

RELATIVE LDH RELEASE
OXYGEN GLUCOSE DEPRIVATION
MIK801 + CNQX + NIMODIPINE
pH 7.4
pH 6.0
pH 6.0 + PcTX VENOM
pH 6.0 + L-NAME
pH 6.0 + TROLAX
ASIC1-/-
**
*

Fig. 13
| | VARIANT | IDENTIFIER | POSITION ----1----2----3----4 |
|---|---|---|---|
| 50 | FULL LENGTH PcTx1 | (SEQ ID:1): | EDCIPKWKGCVNRHGDCCEGLECWKRRRSFEVCVPKTPKT |
| 70 | N-TERMINAL DEL. | (SEQ ID:2): | CIPKWKGCVNRHGDCCEGLECWKRRRSFEVCVPKTPKT |
| 72 | C-TERMINAL DEL. | (SEQ ID:3): | EDCIPKWKGCVNRHGDCCEGLECWKRRRSFEVCVPKT |
| 74 | FULL C-TERMINAL DEL. | (SEQ ID:4): | EDCIPKWKGCVNRHGDCCEGLECWKRRRSFEVC |
| 76 | N & C -TERMINAL DEL. | (SEQ ID:5): | CIPKWKGCVNRHGDCCEGLECWKRRRSFEVC |
Fig. 14
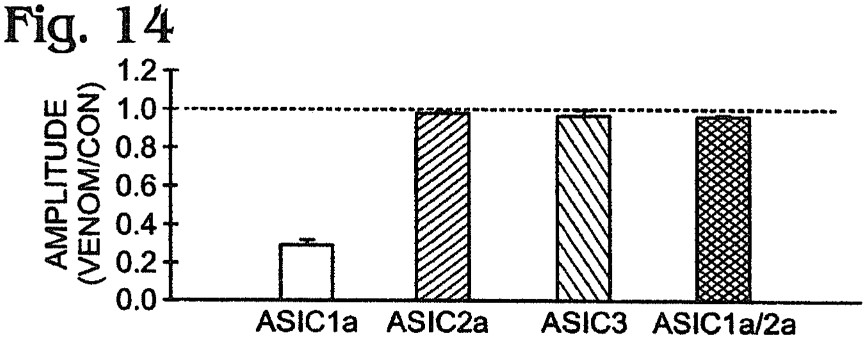
Fig. 15
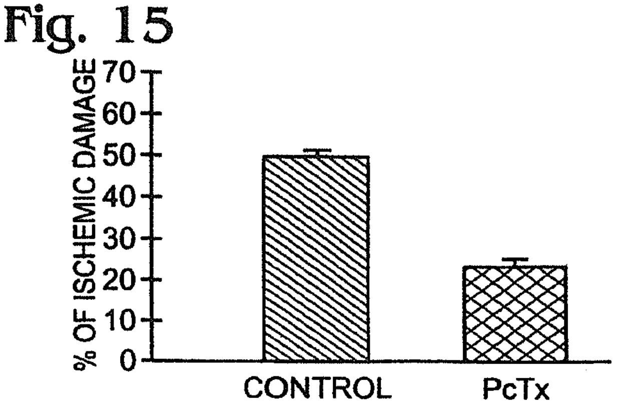

SEQUENCE LISTING

```
<160> NUMBER OF SEQ ID NOS: 5

<210> SEQ ID NO 1
<211> LENGTH: 40
<212> TYPE: PRT
<213> ORGANISM: Psalmopoeus cambridgei
<300> PUBLICATION INFORMATION:
<301> AUTHORS: Escoubas, P. et al.
<302> TITLE: Isolation of a tarantula toxin specific for a class of
      proton-gated Na+ channels
<303> JOURNAL: J. Biol. Chem.
<304> VOLUME: 275
<306> PAGES: 25116-25121
<307> DATE: 2000
<308> DATABASE ACCESSION NUMBER: Swissprot P60514
<309> DATABASE ENTRY DATE: 2004-03-29
<313> RELEVANT RESIDUES IN SEQ ID NO: (1)..(40)

<400> SEQUENCE: 1

Glu Asp Cys Ile Pro Lys Trp Lys Gly Cys Val Asn Arg His Gly Asp
1               5                   10                  15

Cys Cys Glu Gly Leu Glu Cys Trp Lys Arg Arg Arg Ser Phe Glu Val
            20                  25                  30

Cys Val Pro Lys Thr Pro Lys Thr
        35                  40


<210> SEQ ID NO 2
<211> LENGTH: 38
<212> TYPE: PRT
<213> ORGANISM: Artificial Sequence
<220> FEATURE:
<223> OTHER INFORMATION: Deletion derivative of PcTx1 (SEQ ID NO:1)

<400> SEQUENCE: 2

Cys Ile Pro Lys Trp Lys Gly Cys Val Asn Arg His Gly Asp Cys Cys
1               5                   10                  15

Glu Gly Leu Glu Cys Trp Lys Arg Arg Arg Ser Phe Glu Val Cys Val
            20                  25                  30

Pro Lys Thr Pro Lys Thr
        35
```

-continued

```
<210> SEQ ID NO 3
<211> LENGTH: 37
<212> TYPE: PRT
<213> ORGANISM: Artificial Sequence
<220> FEATURE:
<223> OTHER INFORMATION: Deletion derivative of PcTx1 (SEQ ID NO:1)

<400> SEQUENCE: 3

Glu Asp Cys Ile Pro Lys Trp Lys Gly Cys Val Asn Arg His Gly Asp
1               5                   10                  15

Cys Cys Glu Gly Leu Glu Cys Trp Lys Arg Arg Arg Ser Phe Glu Val
            20                  25                  30

Cys Val Pro Lys Thr
        35


<210> SEQ ID NO 4
<211> LENGTH: 33
<212> TYPE: PRT
<213> ORGANISM: Artificial Sequence
<220> FEATURE:
<223> OTHER INFORMATION: Deletion derivative of PcTx1 (SEQ ID NO:1)

<400> SEQUENCE: 4

Glu Asp Cys Ile Pro Lys Trp Lys Gly Cys Val Asn Arg His Gly Asp
1               5                   10                  15

Cys Cys Glu Gly Leu Glu Cys Trp Lys Arg Arg Arg Ser Phe Glu Val
            20                  25                  30

Cys


<210> SEQ ID NO 5
<211> LENGTH: 31
<212> TYPE: PRT
<213> ORGANISM: Artificial Sequence
<220> FEATURE:
<223> OTHER INFORMATION: Deletion derivative of PcTx1 (SEQ ID NO:1)

<400> SEQUENCE: 5

Cys Ile Pro Lys Trp Lys Gly Cys Val Asn Arg His Gly Asp Cys Cys
1               5                   10                  15

Glu Gly Leu Glu Cys Trp Lys Arg Arg Arg Ser Phe Glu Val Cys
            20                  25                  30
```

TREATMENT OF ISCHEMIA

This application is a continuation application of U.S. patent application Ser. No. 15/167,702, filed May 27, 2016, which is a continuation application of U.S. patent application Ser. No. 14/660,581, filed Mar. 17, 2015, which is a continuation application of U.S. patent application Ser. No. 13/284,166, filed Oct. 28, 2011, now U.S. Pat. No. 9,745,356, which is a continuation application of the U.S. patent application Ser. No. 11/724,859, filed Mar. 16, 2007, now U.S. Pat. No. 8,076,450, which claims priority to U.S. Provisional Patent Application No. 60/611,241, filed Sep. 16, 2004. The entirety of all of the aforementioned applications is incorporated herein by reference.

GOVERNMENT LICENSE RIGHTS

This invention was made with U.S. Government support under grant R21 NS42799 from the National Institutes of Health. The U.S. Government thus may have certain license rights in this invention.

This application was made with government support under certain grants awarded by the NIH. The government has certain rights in the application.

BACKGROUND

Strokes may be caused by a disruption of blood flow to the brain, for example, due to a clot or a leak in a blood vessel that supplies the brain with blood. This disruption of blood flow deprives brain tissue of oxygen, often resulting in localized death of brain tissue (focal infarction) and thus permanent damage to the brain.

Changes in the ion flux into neurons may lead to the cell death produced by stroke. Accordingly, various ion channels may be candidates for mediating this altered ion flux, thus confounding the search for a suitable therapeutic target.

SUMMARY

The present teachings provide a system, including methods and compositions, for treatment of ischemia.

BRIEF DESCRIPTION OF THE DRAWINGS

FIG. 13 is a comparative view of the cystine knot peptide of FIG. 12 aligned with various exemplary deletion derivatives of the peptide, in accordance with aspects of the present teachings.

FIG. 14 is an exemplary graph plotting the amplitude of calcium current measured in cells as a function of the ASIC family member(s) expressed in the cells, in accordance with aspects of the present teachings.

FIG. 15 is a graph presenting exemplary data related to the efficacy of nasally administered PcTx venom in reducing ischemic injury in an animal model system, in accordance with aspects of the present teachings.

DETAILED DESCRIPTION

The present teachings provide a system, including methods and compositions, for treatment of ischemia. The methods may include approaches for reducing injury resulting from ischemia and/or for identifying drugs for ischemia treatment. The methods selectively may inhibit one or more members of the acid sensing ion channel (ASIC) family, to provide a targeted therapy for ischemia treatment.

Figure 1:
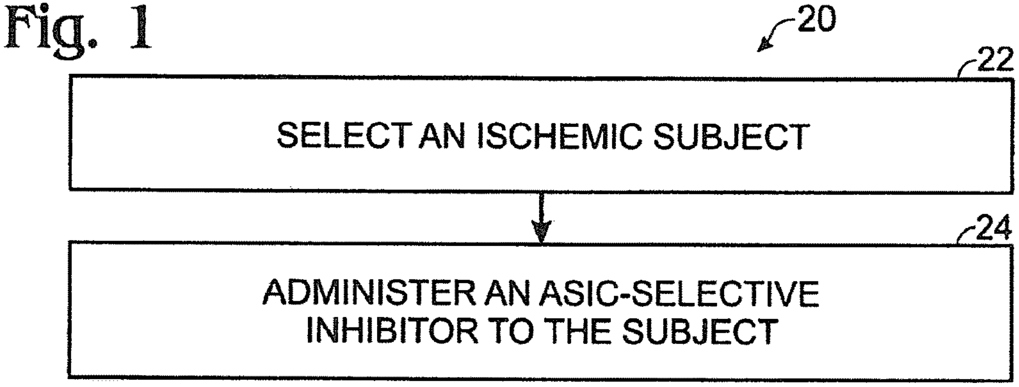
FIG. 1 is a view of a flowchart illustrating an exemplary method of treating ischemia, in accordance with aspects of the present teachings.

FIG. 1 shows a flowchart 20 with exemplary steps 22, 24 that may be performed in a method of treating ischemia. The steps may be performed any suitable number of times and in any suitable combination. In the method, an ischemic subject (or subjects) may be selected for treatment, indicated at 22. An ASIC-selective inhibitor then may be administered to the ischemic subject(s), indicated at 24. Administration of the inhibitor to the ischemic subject may be in a therapeutically effect amount, to reduce ischemia-induced injury to the subject, for example, reducing the amount of brain damage resulting from a stroke.

A potential explanation for the efficacy of the ischemia treatment of FIG. 1 may be offered by the data of the present teachings (e.g., see Example 1). In particular, the damaging effects of ischemia may not be equal to acidosis, that is, acidification of tissue/cells via ischemia may not be sufficient to produce ischemia-induced injury. Instead, ischemia-induced injury may be caused, in many cases, by calcium flux into cells mediated by a member(s) of the ASIC family, particularly ASIC1a. Accordingly, selective inhibition of the channel activity of ASIC 1a may reduce this harmful calcium flux, thereby reducing ischemia-induced injury.

Figure 2:
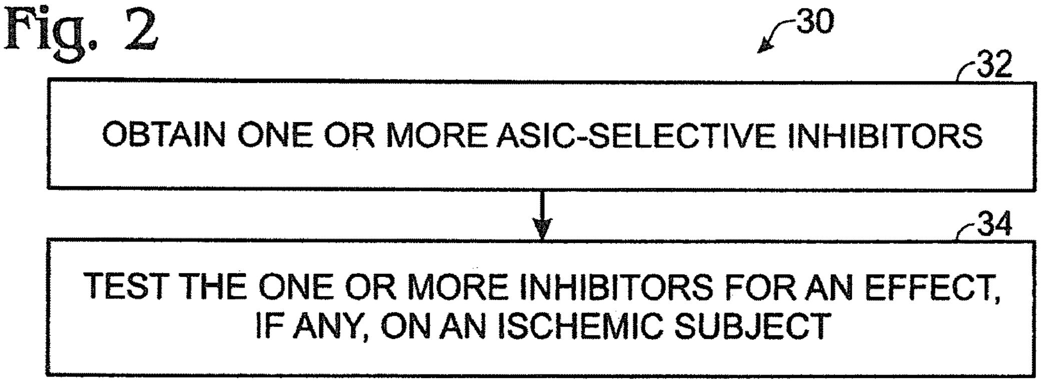
FIG. 2 is a view of a flowchart illustrating an exemplary method of identifying drugs for treating ischemia, in accordance with aspects of the present teachings.
Figure 3A:
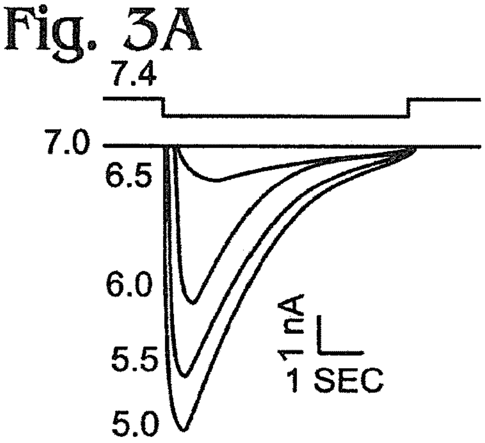
FIGS. 3A-3D are a series of graphs presenting exemplary data related to the electrophysiology and pharmacology of acid sensing ion channel (ASIC) proteins in cultured mouse cortical neurons, in accordance with aspects of the present teachings.
Figure 3B:
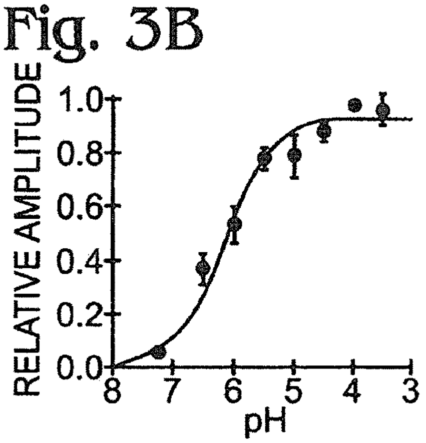
Figure 3C:
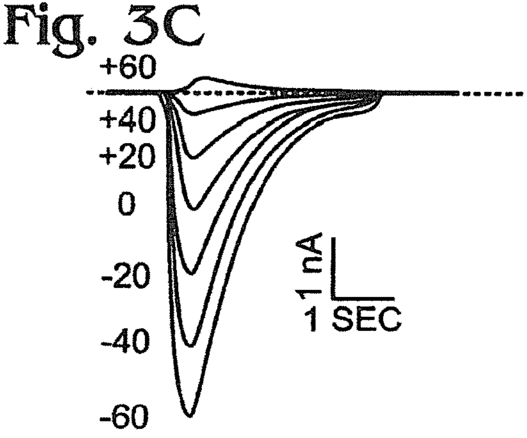
Figure 3D:
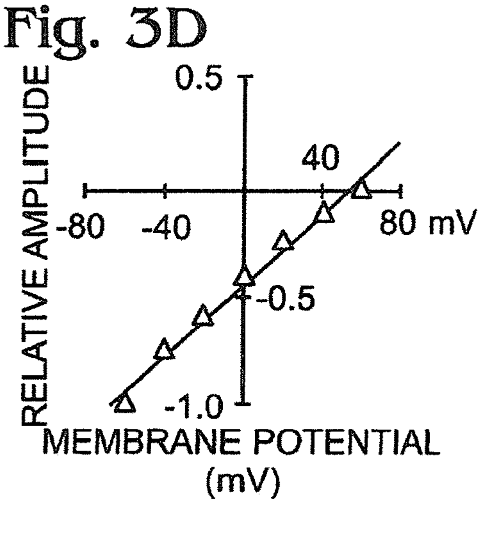
Figure 4A:
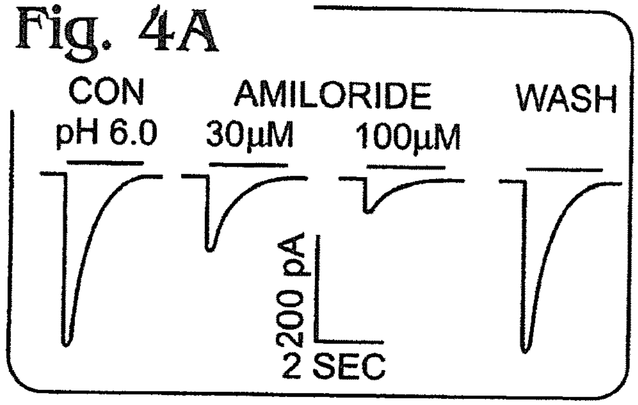
FIGS. 4A-4D are an additional series of graphs presenting exemplary data related to the electrophysiology and pharmacology of ASIC proteins in cultured mouse cortical neurons, in accordance with aspects of the present teachings.
Figure 4B:
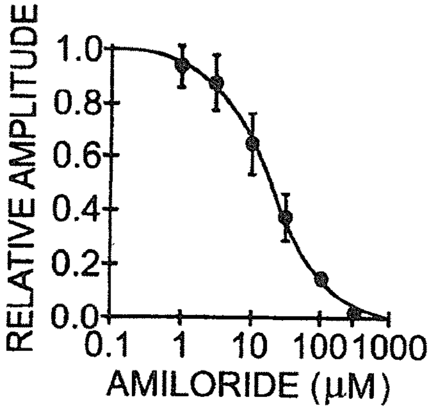
Figure 4C:
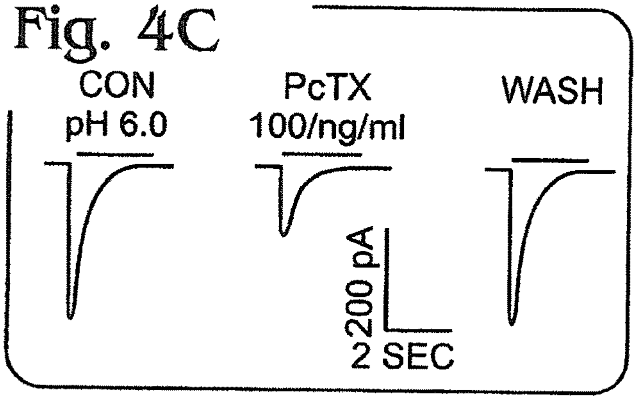
Figure 4D:
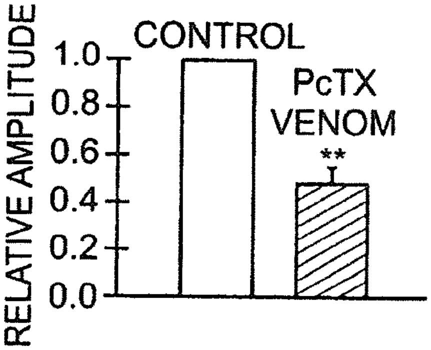

FIG. 2 shows a flowchart 30 with exemplary steps 32, 34 that may be performed in a method of identifying drugs for treatment of ischemia. The steps may be performed any suitable number of times and in any suitable combination. In the method, one or more ASIC-selective inhibitors may be obtained, indicated at 32. The inhibitors then may be tested on an ischemic subject for an effect on ischemia-induced injury, indicated at 34.

The methods of the present teachings may provide one or more advantages over other methods of ischemia treatment. These advantages may include (1) less ischemia-induced injury, (2) fewer side effects of treatment (e.g., due to selection of a more specific therapeutic target), and/or (3) a longer time window for effective treatment, among others.

Further aspects of the present teachings are described in the following sections, including (I) ischemia, (II) ischemic subjects and subject selection, (III) ASIC inhibitors, (IV) administration of inhibitors, (V) identification of drugs, and (VI) examples.

1. Ischemia

The system of the present teachings is directed to treatment of any suitable ischemia. Ischemia, as used herein, is a reduced blood flow to an organ(s) and/or tissue(s). The reduced blood flow may be caused by any suitable mechanism including a partial or complete blockage (an obstruction), a narrowing (a constriction), and/or a leak/rupture, among others, of one or more blood vessels that supply blood to the organ(s) and/or tissue(s). Accordingly, ischemia may be created by thrombosis, an embolism, atherosclerosis, hypertension, hemorrhage, an aneurysm, surgery, trauma, medication, and/or the like. The reduced blood flow thus may be chronic, transient, acute, sporadic, and/or the like.

Any suitable organ or tissue may experience a reduced blood flow in the ischemia being treated. Exemplary organs and/or tissues may include the brain, arteries, the heart, intestines, the eye (e.g., the optic nerve), etc. Ischemia-induced injury (i.e., disease and/or damage) produced by various ischemias may include ischemic myelopathy, ischemic optic neuropathy, ischemic colitis, coronary heart disease, and/or cardiac heart disease (e.g., angina, heart attack, etc.), among others. Ischemia-induced injury thus may damage and/or kill cells and/or tissue, for example, producing necrotic (infarcted) tissue, inflammation, and/or tissue remodeling, among others, at affected sites within the body. Treatment according to aspects of the present teachings may reduce the incidence, extent, and/or severity of this injury.

The system of the present teachings may provide treatment of stroke. Stroke, as used herein, is brain ischemia produced by a reduced blood supply to a part (or all) of the brain. Symptoms produced by stroke may be sudden (such as loss of consciousness) or may have a gradual onset over hours or days. Furthermore, the stroke may be a major ischemic attack (a full stroke) or a more minor, transient ischemic attack, among others. Symptoms produced by stroke may include, for example, hemiparesis, hemiplegia, one-sided numbness, one-sided weakness, one-sided paralysis, temporary limb weakness, limb tingling, confusion, trouble speaking, trouble understanding speech, trouble seeing in one or both eyes, dim vision, loss of vision, trouble walking, dizziness, a tendency to fall, loss of coordination, sudden severe headache, noisy breathing, and/or loss of consciousness. Alternatively, or in addition, the symptoms may be detectable more readily or only via tests and/or instruments, for example, an ischemia blood test (e.g., to test for altered albumin, particular protein isoforms, damaged proteins, etc.), an electrocardiogram, an electroencephalogram, an exercise stress test, and/or the like.

II. ISCHEMIC SUBJECTS AND SUBJECT SELECTION

The system of the present teachings may provide treatment of ischemic subjects to reduce ischemic injury to the subjects. An ischemic subject, as used herein, is any person (a human subject) or animal (an animal subject) that has ischemia, an ischemia-related condition, a history of ischemia, and/or a significant chance of developing ischemia after treatment begins and during a time period in which the treatment is still effective.

The ischemic subject may be an animal. The term "animal," as used herein, refers to any animal that is not human. Exemplary animals that may be suitable include any animal with a bloodstream, such as rodents (mice, rats, etc.), dogs, cats, birds, sheep, goats, non-human primates, etc. The animal may be treated for its own sake, e.g., for veterinary purposes (such as treatment of a pet). Alternatively, the animal may provide an animal model of ischemia, to facilitate testing drug candidates for human use, such as to determine the candidates' potency, window of effectiveness, side effects, etc. Further aspects of testing performed with animal model systems are described below in Section V.

An ischemia-related condition may be any consequence of ischemia. The consequence may be substantially concurrent with the onset ischemia (e.g., a direct effect of the ischemia) and/or may occur substantially after ischemia onset and/or even after the ischemia is over (e.g., an indirect, downstream effect of the ischemia, such reperfusion of tissue when ischemia ends). Exemplary ischemia-related conditions may include any combination of the symptoms (and/or conditions) listed above in Section I. Alternatively, or in addition, the symptoms may include local and/or systemic acidosis (pH decrease), hypoxia (oxygen decrease), free radical generation, and/or the like.

Ischemic subjects for treatment may be selected by any suitable criteria. Exemplary criteria may include any detectable symptoms of ischemia, a history of ischemia, an event that increases the risk of (or induces) ischemia (such as a surgical procedure, trauma, administration of a medication, etc.), and/or the like. A history of ischemia may involve one or more prior ischemic episodes. In some examples, a subject selected for treatment may have had an onset of ischemia that occurred at least about one, two, or three hours before treatment begins, or a plurality of ischemic episodes (such as transient ischemic attacks) that occurred less than about one day, twelve hours, or six hours prior to initiation of treatment.

III. ASIC INHIBITORS

Inhibitors of ASIC family members, as used herein, are substances that reduce (partially, substantially, or completely block) the activity or one or more members of the ASIC family, that is, ASIC1a, ASIC1b, ASIC2a, ASIC2b, ASIC3, and ASIC4, among others. In some examples, the inhibitors may reduce the channel activity of one or more members, such as the ability of the members to flux ions (e.g., sodium, calcium, and/or potassium ions, among others) through cell membranes (into and/or out of cells). The substances may be compounds (small molecules of less than about 10 kDa, peptides, nucleic acids, lipids, etc.), complexes of two or more compounds, and/or mixtures, among others. Furthermore, the substances may inhibit ASIC family members by any suitable mechanism including competitive, noncompetitive, uncompetitive, and/or mixed inhibition, among others.

The inhibitor may be an ASIC1a inhibitor that inhibits acid sensing ion channel 1a (ASIC1a). ASIC1a, as used herein, refers to an ASIC1a protein or channel from any species. For example, an exemplary human ASIC1a protein/channel is described in Waldmann, R., et al. 1997, Nature 386, pp. 173-177, which is incorporated herein by reference.

The expression "ASIC1a inhibitor" may refer to a product which, within the scope of sound pharmacological judgment, is potentially or actually pharmaceutically useful as an inhibitor of ASIC1a, and includes reference to substances which comprise a pharmaceutically active species and are described, promoted, or authorized as an ASIC1a inhibitor.

An ASIC1a inhibitor may be selective within the ASIC family. Selective inhibition of ASIC1a, as used herein, is inhibition that is substantially stronger on ASIC1a than on another ASIC family member(s) when compared (for example, in cultured cells) after exposure of each to the same (sub-maximal) concentration(s) of an inhibitor. The inhibitor may inhibit ASIC1a selectively relative to at least one other ASIC family member (ASIC1b, ASIC2a, ASIC2b, ASIC3, ASIC 4, etc.) and/or selectively relative to every other ASIC family member. The strength of inhibition for a selective inhibitor may be described by an inhibitor concentration at which inhibition occurs (e.g., an IC.sub.50 (inhibitor concentration that produces 50% of maximal inhibition) or a K.sub.i value (inhibition constant or dissociation constant)) relative to different ASIC family members. An ASIC1a-selective inhibitor may inhibit ASIC1a activity at a concentration that is at least about two-, four-, or ten-fold lower (one-half, one-fourth, or one-tenth the concentration or lower) than for inhibition of at least one other or of every other ASIC family member. Accordingly, an ASIC1a-selective inhibitor may have an IC.sub.50 and/or K.sub.i for ASIC1a inhibition that is at least about two-, four-, or ten-fold lower (one-half, one-fourth, or one-tenth or less) than for inhibition of at least one other ASIC family member and/or for inhibition of every other ASIC family member.

An ASIC1a-selective inhibitor, in addition to being selective, also may be specific for ASIC1a. ASIC1a-specific inhibition, as used herein, is inhibition that is substantially exclusive to ASIC1a relative to every other ASIC family member. An ASIC1a-specific inhibitor may inhibit ASIC1a at an inhibitor concentration that is at least about twenty-fold lower (5% of the concentration or less) than for inhibition of every other ASIC family member. Accordingly, an ASIC1a-specific inhibitor may have an $IC_{50}$ and/or $K_i$ for ASIC1a relative to every other member of the ASIC family that is at least about twenty-fold lower (five percent or less), such that, for example, inhibition of other ASIC family members is at least substantially (or completely) undetectable.

Any suitable ASIC inhibitor or combination of inhibitors may be used. For example, a subject may be treated with an ASIC1a-selective inhibitor and a nonselective ASIC inhibitor, or with an ASIC1a-selective inhibitor and an inhibitor to a non-ASIC channel protein, such as a non-ASIC calcium channel. In some examples, a subject may be treated with an ASIC1a-selective inhibitor and an inhibitor of NMDA receptors, such as a glutamate antagonist.

The inhibitor may be or include a peptide. The peptide may have any suitable number of amino acid subunits, generally at least about ten and less than about one-thousand subunits. In some examples, the peptide may have a cystine knot motif. A cystine knot, as used herein, generally comprises an arrangement of six or more cysteines. A peptide with these cysteines may create a "knot" including (1) a ring formed by two disulfide bonds and their connecting backbone segments, and (2) a third disulfide bond that threads through the ring. In some examples, the peptide may be a conotoxin from an arachnid and/or cone snail species. For example, the peptide may be PcTx1 (psalmotoxin 1), a toxin from a tarantula (*Psalmopoeus cambridgei* (Pc)).

In some examples, the peptide may be structurally related to PcTx1, such that the peptide and PcTx1 differ by at least one deletion, insertion, and/or substitution of one or more amino acids. For example, the peptide may have at least about 25% or at least about 50% sequence identity, and/or at least about 25% or at least about 50% sequence similarity with PcTx1 (see below). Further aspects of peptides that may be suitable as inhibitors are described below in Example 3.

Methods of alignment of amino acid sequences for comparison and generation of identity and similarity scores are well known in the art. Exemplary alignment methods that may be suitable include (Best Fit) of Smith and Waterman, a homology alignment algorithm (GAP) of Needleman and Wunsch, a similarity method (Tfasta and Fasta) of Pearson and Lipman, and/or the like. Computer algorithms of these and other approaches that may be suitable include, but are not limited to: CLUSTAL, GAP, BESTFIT, BLASTP, FASTA, and TFASTA.

As used herein, "sequence identity" or "identity" in the context of two peptides relates to the percentage of residues in the corresponding peptide sequences that are the same when aligned for maximum correspondence. In some examples, peptide residue positions that are not identical may differ by conservative amino acid substitutions, where amino acid residues are substituted for other amino acid residues with similar chemical properties (e.g. charge or hydrophobicity) and therefore are expected to produce a smaller (or no) effect on the functional properties of the molecule. Where sequences differ in conservative substitutions, the percent sequence identity may be adjusted upwards, to give a "similarity" of the sequences, which corrects for the conservative nature of the substitutions. For example, each conservative substitution may be scored as a partial rather than a full mismatch, thereby correcting the percentage sequence identity to provide a similarity score. The scoring of conservative substitutions to obtain similarity scores is well known in the art and may be calculated by any suitable approach, for example, according to the algorithm of Meyers and Miller, Computer Applic. Biol Sci., 4: 11-17 (1988), e.g., as implemented in the program PC/GENE (Intelligenetics, Mountain View, Calif., USA).

IV. ADMINISTRATION OF INHIBITORS

Administration (or administering), as used herein, includes any route of subject exposure to an inhibitor, under any suitable conditions, and at any suitable time(s). Administration may be self-administration or administration by another, such as a health-care practitioner (e.g., a doctor, a nurse, etc.). Administration may be by injection (e.g., intravenous, intramuscular, subcutaneous, intracerebral, epidural, and/or intrathecal, among others), ingestion (e.g., using a capsule, lozenge, a fluid composition, etc.), inhalation (e.g., an aerosol (less than about 10 microns average droplet diameter) inhaled nasally and/or orally), absorption through the skin (e.g., with a skin patch) and/or mucosally (e.g., through oral, nasal, and/or pulmonary mucosa, among others), and/or the like. Mucosal administration may be achieved, for example, using a spray (such as a nasal spray), an aerosol that is inhaled), and/or the like. A spray may be a surface spray (droplets on average greater than about 50 microns in diameter) and/or a space spray (droplets on average about 10-50 microns in diameter). In some examples, ischemia may produce an alteration of the blood-brain barrier of an ischemic subject, thus increasing the efficiency with which an inhibitor that is introduced (e.g., by injection and/or absorption) into the bloodstream of a subject can reach the brain. Administration may be performed once or a plurality of times, and at any suitable time relative to ischemia diagnosis, to provide treatment. Accordingly, administration may be performed before ischemia has been detected (e.g., prophylactically) after a minor ischemic episode, during chronic ischemia, after a full stroke, and/or the like.

A therapeutically effective amount of an inhibitor may be administered. A therapeutically effective amount of an inhibitor, as used herein, is any amount of the inhibitor that, when administered to subjects, reduces, in a significant number of the subjects, the degree, incidence, and/or extent of ischemia-induced injury in the subjects. Accordingly, a therapeutically effective amount may be determined, for example, in clinical studies in which various amounts of the inhibitor are administered to test subjects (and, generally, compared to a control group of subjects).

The inhibitor may be administered in any suitable form and in any suitable composition to subjects. In some examples, the inhibitor may be configured as a pharmaceutically acceptable salt. The composition may be formulated to include, for example, a fluid carrier/solvent (a vehicle), a preservative, one or more excipients, a coloring agent, a flavoring agent, a salt(s), an anti-foaming agent, and/or the like. The inhibitor may be present at a concentration in the vehicle that provides a therapeutically effective amount of the inhibitor for treatment of ischemia when administered to an ischemic subject.

V. IDENTIFICATION OF DRUGS

Additional ASIC inhibitors may be identified for use as drugs to treat ischemia. Identification may include (A) obtaining one or more ASIC inhibitors, and (B) testing the ASIC inhibitors on ischemic subjects.

A. Obtaining ASIC Inhibitors

One or more ASIC inhibitors, particularly ASIC1a inhibitors as described above, may be obtained. The inhibitors may be obtained by any suitable approach, such by screening a set of candidate inhibitors (e.g., a library of two or more compounds) and/or by rationale design, among others.

Screening may involve any suitable assay system that measures interaction between ASIC proteins and the set of candidate inhibitors. Exemplary assay systems may include assays performed biochemically (e.g., binding assays), with cells grown in culture ("cultured cells"), and/or with organisms, among others.

A cell-based assay system may measure an effect, if any, of each candidate inhibitor on ion flux in the cells, generally acid-sensitive ion flux. In some examples, the ion flux may be a flux of calcium and/or sodium, among others. The assay system may use cells expressing an ASIC family member, such as ASIC1a, or two or more distinct sets of cells expressing two or more distinct ASIC family members, such as ASIC1a and another ASIC family member(s), to determine the selectivity of each inhibitor for these family members. The cells may express each ASIC family member endogenously or through introduction of foreign nucleic acid. In some examples, the assay system may measure ion flux electrophysiologically (such as by patch clamp), using an ion-sensitive or membrane potential-sensitive dye (e.g., a calcium sensitive dye such as Fura-2), or via a gene-based reporter system that is sensitive to changes in membrane potential and/or intracellular ion (e.g., calcium) concentrations, among others. The assay system may be used to test candidate inhibitors for selective and/or specific inhibition of ASIC family members, particularly ASIC1a.

B. Testing ASIC Inhibitors on Subjects

One or more ASIC inhibitors may be administered to an ischemic subject(s) to test the efficacy of the inhibitors for treatment of ischemia. The ischemic subjects may be people or animals. In some examples, the ischemic subjects may provide an animal model system of ischemia and/or stroke. Exemplary animal model systems include rodents (mice and/or rats, among others) with ischemia induced experimentally. The ischemia may be induced mechanically (e.g., surgically) and/or by administration of a drug, among others. In some examples, the ischemia may be induced by occlusion of a blood vessel, such as by constriction of a mid-cerebral artery.

VI. EXAMPLES

The following examples describes selected aspects and embodiments of the present teachings, particularly data describing in vitro and in vivo effects of ASIC inhibition, and exemplary cystine knot peptides for use as inhibitors. These examples are intended for the purposes of illustration and should not be construed to limit the scope of the present teachings.

Example 1

Neuroprotection in Ischemia Blocking Calcium-Permeable Acid-Sensing Ion Channels This example describes experiments showing a role of ASIC1a in mediating ischemic injury and the ability ASIC1a inhibitors to reduce ischemic injury; see FIGS. 2-10.

Overview $Ca^2$+ toxicity may play a central role in ischemic brain injury. The mechanism by which toxic $Ca^2$+ loading of cells occurs in the ischemic brain has become less clear as multiple human trials of glutamate antagonists have failed to show effective neuroprotection in stroke. Acidosis may be a common feature of ischemia and may play a critical role in brain injury; however, the mechanism(s) remains ill defined. Here, we show that acidosis may activate $Ca^2$+-permeable acid-sensing ion channels (ASICs), which may induce glutamate receptor-independent, $Ca^2$+-dependent, neuronal injury inhibited by ASIC blockers. Cells lacking endogenous ASICs may be resistant to acid injury, while transfection of $Ca^2$+-permeable ASIC1a may establish sensitivity. In focal ischemia, intracerebroventricular injection of ASIC1a blockers or knockout of the ASIC1a gene may protect the brain from ischemic injury and may do so more potently than glutamate antagonism. Thus, acidosis may injure the brain via membrane receptor-based mechanisms with resultant toxicity of [$Ca^2$+] (intracellular calcium), disclosing new potential therapeutic targets for stroke.

B. Introduction

Intracellular $Ca^2$+ overload may be important for neuronal injury associated with neuropathological syndromes, including brain ischemia (Choi 1995 and Choi 1988a). Excessive $Ca^2$+ in the cell may activate a cascade of cytotoxic events leading to activation of enzymes that break down proteins, lipids, and nucleic acids. NMDA receptors, which may be the most important excitatory neurotransmitter receptors in the central nervous system (McLennan 1983 and Dingledine et al. 1999), have long been considered the main target responsible for $Ca^2$+ overload in the ischemic brain (Simon et al. 1984; Rothman and Olney 1986; Choi 1988b and Meldrum 1995). However, recent clinical efforts to prevent brain injury through the therapeutic use of NMDA receptor antagonists have been disappointing (Lee et al. 1999 and Wahlgren and Ahmed 2004). Although multiple factors, including difficulty in early initiation of treatment, may have contributed to trial failures, glutamate receptor-independent $Ca^2$+ toxicity also or alternatively may be responsible for ischemic brain injury.

The normal brain may require complete oxidation of glucose to fulfill its energy requirements. During ischemia, oxygen depletion may force the brain to switch to anaerobic glycolysis. Accumulation of lactic acid as a byproduct of glycolysis and protons produced by ATP hydrolysis may cause pH to fall in the ischemic brain (Rehncrona 1985 and Siesjo et al. 1996). Consequently, tissue pH typically falls to 6.5-6.0 during ischemia under normoglycemic conditions and may fall below 6.0 during severe ischemia or under hyperglycemic conditions (Nedergaard et al. 1991; Rehncrona 1985 and Siesjo et al. 1996). Nearly all in vivo studies indicate that acidosis aggravates ischemic brain injury (Tombaugh and Sapolsky 1993 and Siesjo et al. 1996). However, the mechanisms of this process remain unclear, although a host of possibilities has been suggested (Siesjo et al. 1996; McDonald et al. 1998; Swanson et al. 1995 and Ying et al. 1999).

Acid-sensing ion channels (ASICs), a newly described class of ligand-gated channels (Waldmann et al. 1997a and Krishtal 2003), have been shown to be expressed throughout neurons of mammalian central and peripheral nervous systems (Waldmann et al. 1997a; Waldmann et al. 1999; Waldmann and Lazdunski 1998; Krishtal 2003; Alvarez de la Rosa et al. 2002 and Alvarez de la Rosa et al. 2003). These channels are members of the degenerin/epithelial sodium channel (Deg/ENaC) superfamily (Benos and Stanton 1999; Bianchi and Driscoll 2002 and Krishtal 2003). Pertinent to ischemia, ASICs also may flux $Ca^2$+ (Waldmann et al. 1997a; Chu et al. 2002 and Yermolaieva et al. 2004).

To date, six ASIC subunits have been cloned. Four of these subunits may form functional homomultimeric channels that are activated by acidic pH to conduct a sodium-selective, amiloride-sensitive, cation current. The pH of half-maximal activation ($pH_{0.5}$) of these channels differs: ASIC1a, $pH_{0.5}$=6.2 (Waldmann et al., 1997a); ASIC1.beta. (also termed ASIC1b), a splice variant of ASIC1a with a unique N-terminal, $pH_{0.5}$=5.9 (Chen et al., 1998); ASIC2a, $pH_{0.5}$=4.4 (Waldmann et al., 1999); and ASIC3, $pH_{0.5}$=6.5 (Waldmann et al., 1997b). Neither ASIC2b nor ASIC4 can form functional homomeric channel (Akopian et al. 2000; Grunder et al. 2000 and Linguеglia et al. 1997), but ASIC2b has been shown to associate with other subunits and modulate their activity (Lingueglia et al., 1997). In addition to Na.sup.+ permeability, homomeric ASIC1a may flux $Ca^2$+ (Waldmann et al. 1997a; Chu et al. 2002 and Yermolaieva et al. 2004). Although the exact subunit composition of ASICs in native neurons has not been determined, both ASIC1a and ASIC2a subunits have been shown to be abundant in the brain (Price et al. 1996; Bassilana et al. 1997; Wemmie et al. 2002 and Alvarez de la Rosa et al. 2003).

Detailed functions of ASICs in both peripheral and central nervous systems remain to be determined. In peripheral sensory neurons, ASICs have been implicated in mechanosensation (Price et al. 2000 and Price et al. 2001) and perception of pain during tissue acidosis (Bevan and Yeats 1991; Krishtal and Pidoplichko 1981; Ugawa et al. 2002; Sluka et al. 2003 and Chen et al. 2002), particularly in ischemic myocardium where ASICs likely transduce anginal pain (Benson et al., 1999). The presence of ASICs in the brain, which lacks nociceptors, suggests that these channels may have functions beyond nociception. Indeed, recent studies have indicated that ASIC1a may be involved in synaptic plasticity, learning/memory, and fear conditioning (Wemmie et al. 2002 and Wemmie et al. 2003). Here, using a combination of patch-clamp recording, $Ca^2$+ imaging, receptor subunit transfection, in vitro cell toxicity assays, and in vivo ischemia models combined with gene knockout, we demonstrate activation of $Ca^2$+-permeable ASIC1a as largely responsible for glutamate-independent, acidosis-mediated, and ischemic brain injury.

C. Results

Acidosis Activates ASICs in Mouse Cortical Neurons

FIGS. 3 and 4 shows exemplary data related to the electrophysiology and pharmacology of ASICs in cultured mouse cortical neurons. FIGS. 3A and 3B are graphs illustrating the pH dependence of ASIC currents activated by a pH drop from 7.4 to the pH values indicated. Dose-response curves were fit to the Hill equation with an average $pH_{0.5}$ of 6.18±0.06 (n=10). FIGS. 3C and 3D are graphs illustrating the current-voltage relationship of ASICs (n=5). The amplitudes of ASIC current at various voltages were normalized to that recorded at −60 mV. FIGS. 4A and 4B are graphs illustrating a dose-dependent blockade of ASIC currents by amiloride. $IC_{50}$=16.4±4.1 μM, N=8. FIGS. 4C and 4D are graphs illustrating a blockade of ASIC currents by PcTX venom. **p<0.01.

We first recorded ASIC currents in cultured mouse cortical neurons, a preparation commonly used for cell toxicity studies (Koh and Choi 1987 and Sattler et al. 1999); see FIG. 3. At a holding potential of −60 mV, a rapid reduction of extracellular pH ($pH_e$) to below 7.0 evoked large transient inward currents with a small steady-state component in the majority of neurons (FIG. 3A). The amplitude of inward current increased in a sigmoidal fashion as $pH_e$ decreased, yielding a $pH_{0.5}$ of 6.18±0.06 (n=10, FIG. 3B). A linear I-V relationship and a reversal close to the $Na^+$ equilibrium potential were obtained (n=6, FIGS. 3C and 3D). These data demonstrate that lowering $pH_e$ may activate typical ASICs in mouse cortical neurons.

We then tested the effect of amiloride, a nonspecific blocker of ASICs (Waldmann et al., 1997a), on the acid-activated currents; see FIG. 4. Similar to previous studies, mainly in sensory neurons (Waldmann et al. 1997a; Benson et al. 1999; Chen et al. 1998 and Varming 1999), amiloride dose-dependently blocked ASIC currents in cortical neurons with an $IC_{50}$ of 16.4±4.1 μM (n=8, FIGS. 4A and 4B). Psalmotoxin 1 (or PcTX1) from venom of the tarantula *Psalmopoeus cambridgei* (PcTX venom) may be a specific ASIC1a blocker (Escoubas et al., 2000). Our studies show that, at a protein concentration of 25 ng/mL, PcTX venom itself may block the current mediated by homomeric ASIC1a expressed in COS-7 cells by 70% (n=4, see Supplemental Figure S1 at Xiong et al., *Neuroprotection in ischemia: blocking calcium-permeable acid-sensing ion channels*, Cell, 118 (2004), pp. 687-698, which is incorporated herein by reference). However, it does not affect currents mediated by heteromeric ASIC1a/2a, homomeric ASIC2a, or ASIC3 channels at 500 ng/mL (n=4-6). In addition, at 500 ng/mL, PcTX venom does not affect the currents through known voltage- and ligand-gated channels, further indicating its specificity for homomeric ASIC1a (n=4-5, Supplemental Figure S2, and Supplemental Data (at the website cited above), which are incorporated herein by reference).

We then tested the effect of PcTX venom on acid-activated current in cortical neurons. At 100 ng/mL, PcTX venom reversibly blocked the peak amplitude of ASIC current by 47%±7% (n=15, FIGS. 4C and 4D), indicating significant contributions of homomeric ASIC1a to total acid-activated currents. Increasing PcTX concentration did not induce further reduction in the amplitude of ASIC current in the majority of cortical neurons (n=8, data not shown), indicating coexistence of PcTX-insensitive ASICs (e.g., heteromeric ASIC1a/2a) in these neurons.

2. ASIC Response is Potentiated by Modeled Ischemia

Figures 5A, 5B, 5C, 5D:
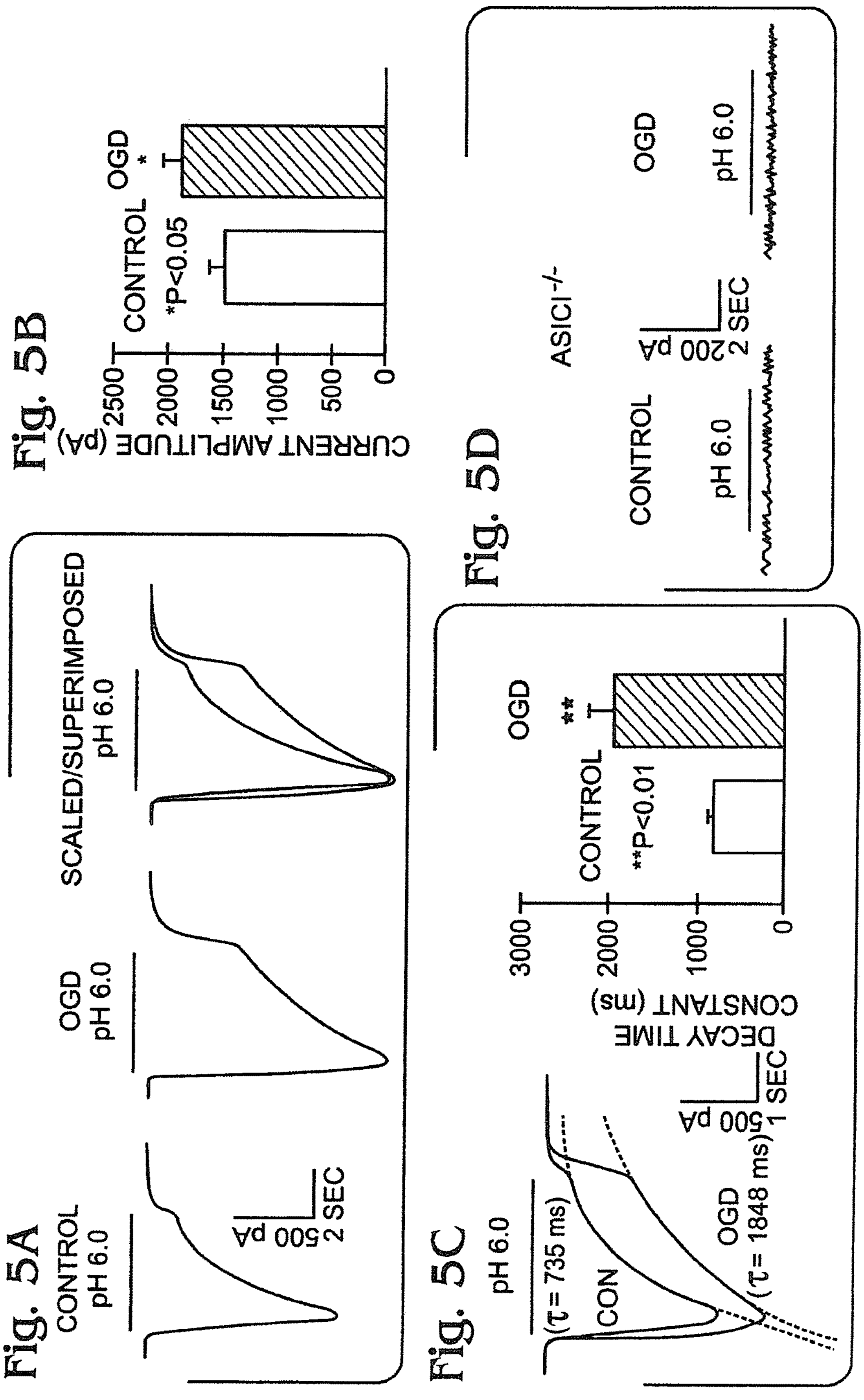
FIGS. 5A-5D are a set of graphs and traces presenting exemplary data showing that modeled ischemia may enhance activity of ASIC proteins, in accordance with aspects of the present teachings.

FIG. 5 shows exemplary data indicating that modeled ischemia may enhance activity of ASICs. FIG. 5A is a series of exemplary traces showing an increase in amplitude and a decrease in desensitization of ASIC currents following 1 hr OGD. FIG. 5B is a graph of summary data illustrating an increase of ASIC current amplitude in OGD neurons. N=40 and 44, *p<0.05. FIG. 5C is a series of exemplary traces and summary data showing decreased ASIC current desensitization in OGD neurons. N=6, p<0.01. FIG. 5**D is a pair of exemplary traces showing lack of acid-activated current at pH 6.0 in ASIC1$^{-/-}$ neurons, in control condition, and following 1 hr OGD (n=12 and 13).

Since acidosis may be a central feature of brain ischemia, we determined whether ASICs may be activated in ischemic conditions and whether ischemia may modify the properties of these channels; see FIG. 5. We recorded ASIC currents in neurons following 1 hr oxygen glucose deprivation (OGD), a common model of in vitro ischemia (Goldberg and Choi, 1993). One set of cultures was washed three times with glucose-free extracellular fluid (ECF) and subjected to OGD, while control cultures were subjected to washes with glucose containing ECF and incubation in a conventional cell culture incubator. OGD was terminated after 1 hr by replacing glucose-free ECF with Neurobasal medium and incubating cultures in the conventional incubator. ASIC current was then recorded 1 hr following the OGD when there was no morphological alteration of neurons. OGD treatment induced a moderate increase of the amplitude of ASIC currents (1520±138 pA in control group, N=44; 1886±185 pA in neurons following 1 hr OGD, N=40, p<0.05, FIGS. 5A and 5B). More importantly, OGD induced a dramatic decrease in ASIC desensitization as demonstrated by an increase in time constant of the current decay (814.7±58.9 ms in control neurons, N=6; 1928.9±315.7 ms in neurons following OGD, N=6, p<0.01, FIGS. 5A and 5C). In cortical neurons cultured from ASIC1$^{-/-}$ mice, reduction of pH from 7.4 to 6.0 did not activate any inward current (n=52), similar to a previous study in hippocampal neurons (Wemmie et al., 2002). In these neurons, 1 hr OGD did not activate or potentiate acid-induced responses (FIG. 5D, n=12 and 13).

3. Acidosis Induces Glutamate-Independent Ca2+ Entry Via ASIC1a

Figure 6B:
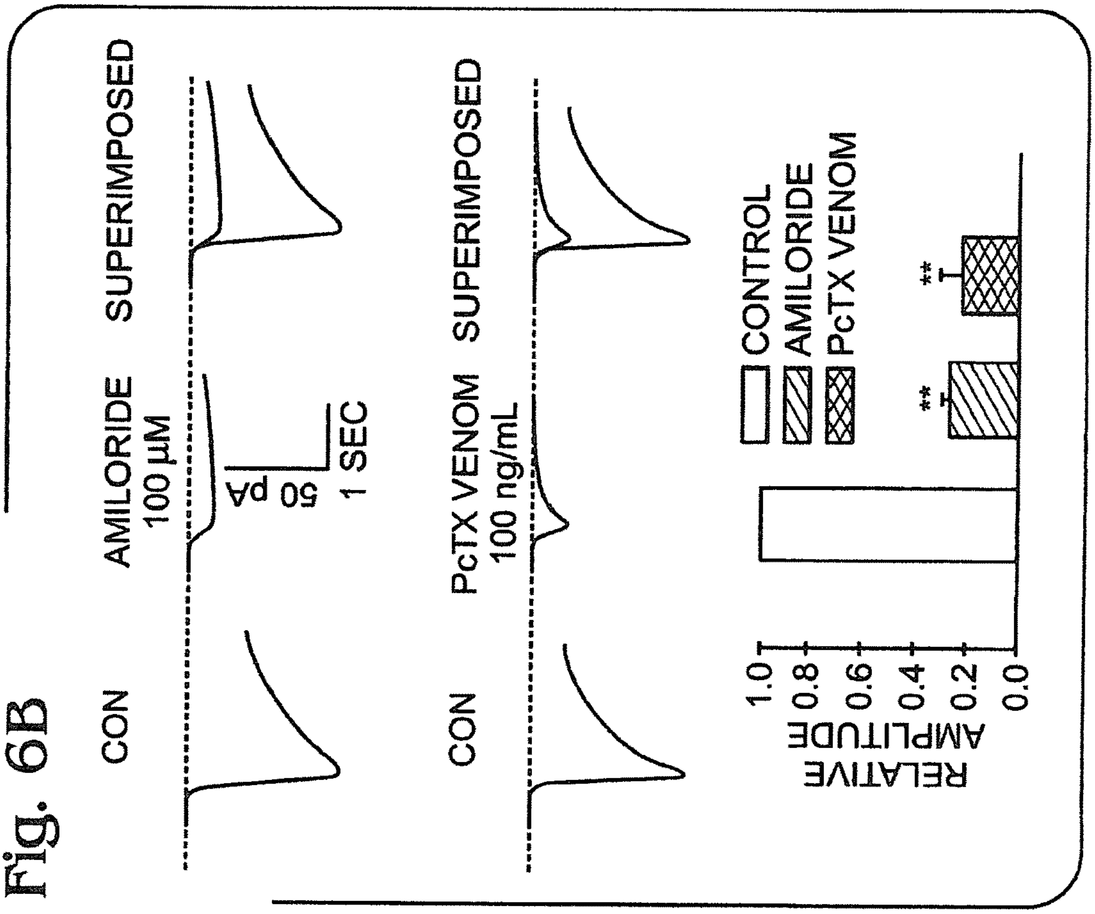
FIGS. 6A-6B and 7A-7D are a set of graphs and traces presenting exemplary data showing that ASIC proteins in cortical neurons may be $Ca^{2+}$ permeable, and that $Ca^{2+}$ permeability may be ASIC1a dependent, in accordance with aspects of the present teachings.
Figure 6A:
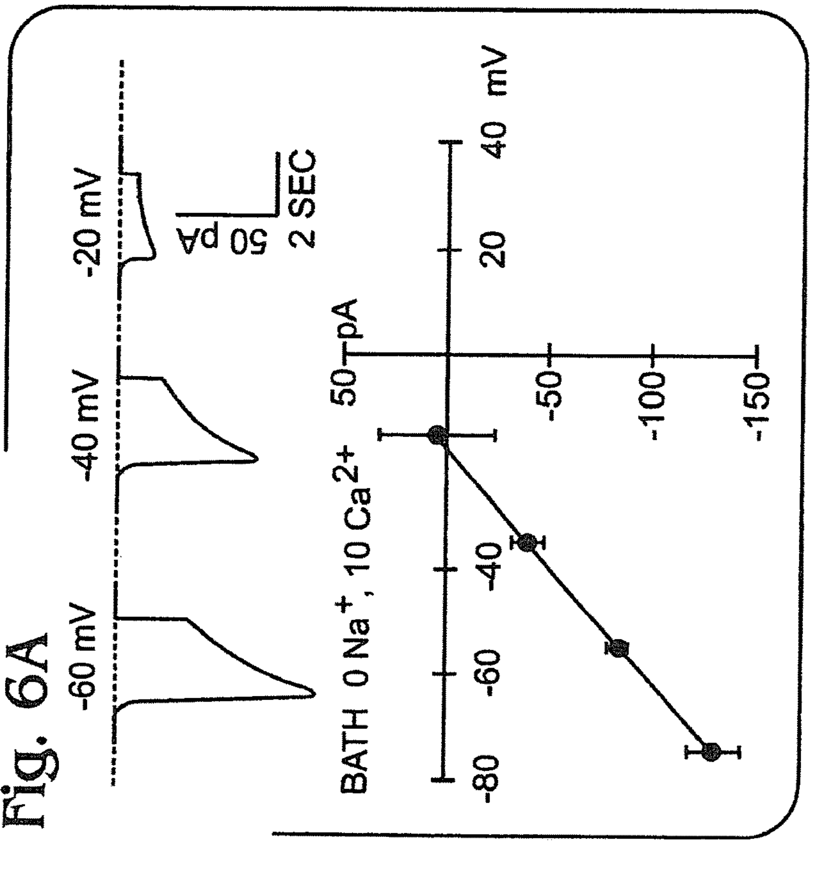
Figures 7A, 7B, 7C, 7D:
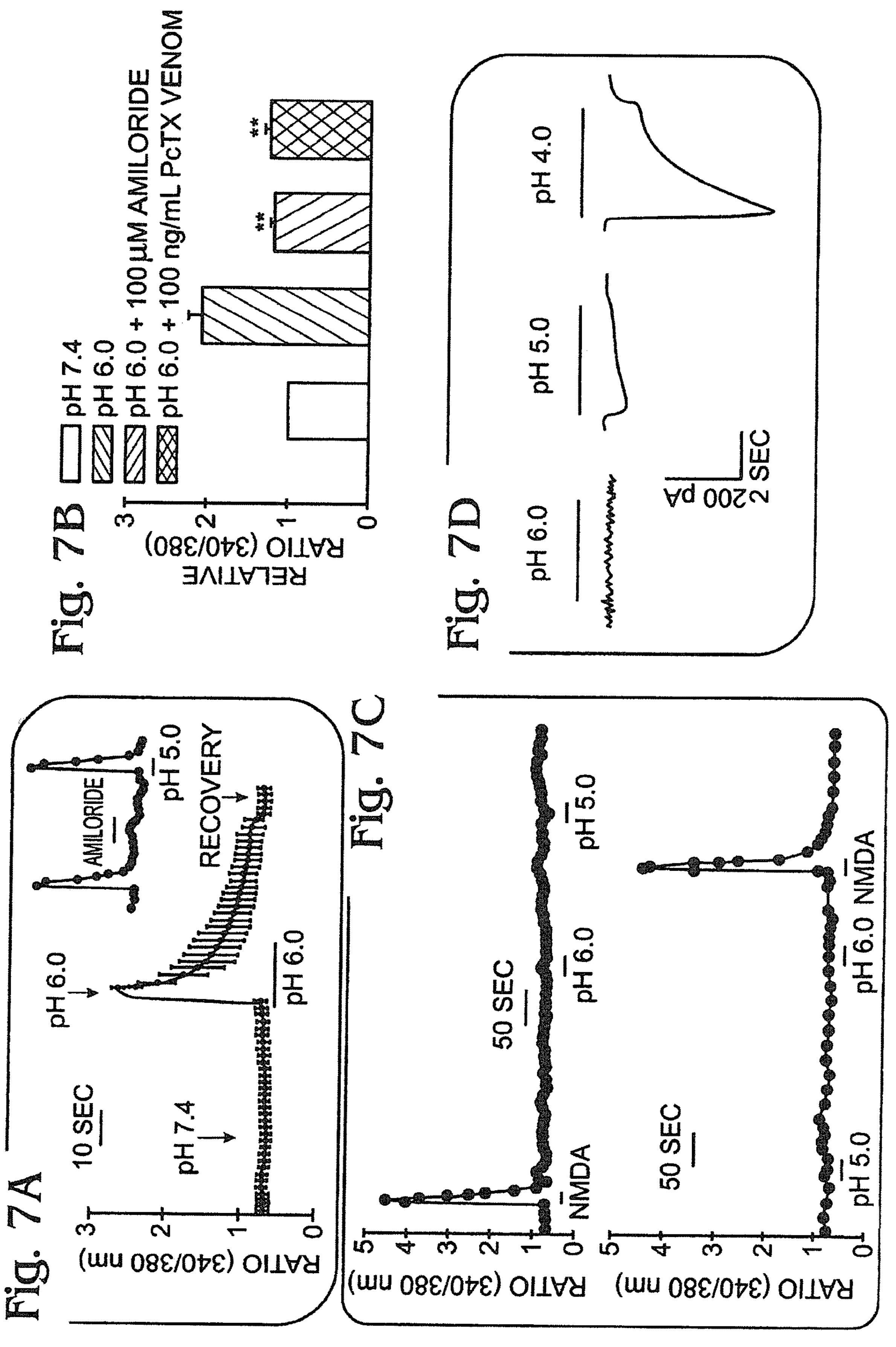

FIGS. 6 and 7 show exemplary data suggesting that ASICs in Cortical Neurons may be $Ca^{2+}$ permeable, and that $Ca^{2+}$ permeability may be ASIC1a dependent. FIG. 6A shows exemplary traces obtained with $Na^+$-free ECF containing 10 mM $Ca^{2+}$ as the only charge carrier. Inward currents were recorded at pH 6.0. The average reversal potential is ~-17 mV after correction of liquid junction potential (n=5). FIG. 6B shows representative traces and summary data illustrating blockade of $Ca^{2+}$ mediated current by amiloride and PcTX venom. The peak amplitude of $Ca^{2+}$ mediated current decreased to 26%±2% of control value by 100 μM amiloride (n=6, p<0.01) and to 22%±0.9% by 100 ng/mL PcTX venom (n=5, p<0.01). FIG. 7A shows exemplary 340/380 nm ratios as a function of pH, illustrating an increase of $[Ca^{2+}]_i$ by pH drop to 6.0. Neurons were bathed in normal ECF containing 1.3 mM $CaCl_2$ with blockers for voltage-gated $Ca^{2+}$ channels (5 μM nimodipine and 1 μM ω-conotoxin MVIIC) and glutamate receptors (10 μM MK801 and 20 μM CNQX). The inset of FIG. 7A shows exemplary inhibition of acid-induced increase of $[Ca^{2+}]_i$ by 100 μM amiloride. FIG. 7B shows exemplary summary data illustrating inhibition of acid-induced increase of $[Ca^{2+}]_i$ by amiloride and PcTX venom. N=6-8, p<0.01 compared with pH 6.0 group. FIG. 7C shows exemplary 340/380 nm ratios as a function of pH and NMDA presence/absence, demonstrating a lack of acid-induced increase of $[Ca^{2+}]_i$ in ASIC1$^{-/-}$ neurons; neurons had a normal response to NMDA (n=8). FIG. 7**D shows exemplary traces illustrating a lack of acid-activated current at pH 6.0 in ASIC1$^{-/-}$ neurons.

Using a standard ion-substitution protocol (Jia et al., 1996) and the Fura-2 fluorescent $Ca^{2+}$-imaging technique (Chu et al., 2002), we determined whether ASICs in cortical neurons are $Ca^{2+}$ permeable; see FIGS. 6 and 7. With bath solutions containing 10 mM $Ca^{2+}$ ($Na^+$ and $K^+$-free) as the only charge carrier and at a holding potential of −60 mV, we recorded inward currents larger than 50 pA in 15 out of 18 neurons, indicating significant $Ca^{2+}$ permeability of ASICs in the majority of cortical neurons (FIG. 6A). Consistent with activation of homomeric ASIC1a channels, currents carried by 10 mM $Ca^{2+}$ were largely blocked by both the nonspecific ASIC blocker amiloride and the ASIC1a-specific blocker PcTX venom (FIG. 6B). The peak amplitude of $Ca^{2+}$-mediated current was decreased to 26%±2% of control by 100 μM amiloride (n=6, p<0.01) and to 22%±0.9% by 100 ng/mL PcTX venom (n=5, p<0.01). $Ca^{2+}$ imaging, in the presence of blockers of other major $Ca^{2+}$ entry pathways (MK801 10 μM and CNQX 20 μM for glutamate receptors; nimodipine 5 μM and ω-conotoxin MVIIC 1 μM for voltage-gated $Ca^{2+}$ channels), demonstrated that 18 out of 20 neurons responded to a pH drop with detectable increases in the concentration of intracellular $Ca^{2+}$ ($[Ca^{2+}]_i$) (FIG. 7A). In general, $[Ca^{2+}]_i$ remains elevated during prolonged perfusion of low pH solutions. In some cells, the $[Ca^{2+}]_i$ increase lasted even longer than the duration of acid perfusion (FIG. 7A). Long-lasting $Ca^{2+}$ responses suggest that ASIC response in intact neurons may be less desensitized than in whole-cell recordings or that $Ca^{2+}$ entry through ASICs may induce subsequent $Ca^{2+}$ release from intracellular stores. Preincubation of neurons with 1.mu.M thapsigargin partially inhibited the sustained component of $Ca^{2+}$ increase, suggesting that $Ca^{2+}$ release from intracellular stores may also contribute to acid-induced intracellular $Ca^{2+}$ accumulation (n=6, data not shown). Similar to the current carried by $Ca^{2+}$ ions (FIG. 6B), both peak and sustained increases in $[Ca^{2+}]_i$ were largely inhibited by amiloride and PcTX venom (FIGS. 7A and 7B, n=6-8), consistent with involvement of homomeric ASIC1a in acid-induced $[Ca^{2+}]_i$ increase. Knockout of the ASICI gene eliminated the acid-induced $[Ca^{2+}]_i$ increase in all neurons without affecting NMDA receptor-mediated $Ca^{2+}$ response (FIG. 7C, n=8). Patch-clamp recordings demonstrated lack of acid-activated currents at pH 6.0 in 52 out of 52 of the ASIC1$^{-/-}$ neurons, consistent with absence of ASIC1a subunits. Lowering pH to 5.0 or 4.0, however, activated detectable current in 24 out of 52 ASIC1$^{-/-}$ neurons, indicating the presence of ASIC2a subunits in these neurons (FIG. 7D). Further electrophysiological studies demonstrated that ASIC1$^{-/-}$ neurons have normal responses for various voltage-gated channels and NMDA, GABA receptor-gated channels (data not shown).

Figure 8A:
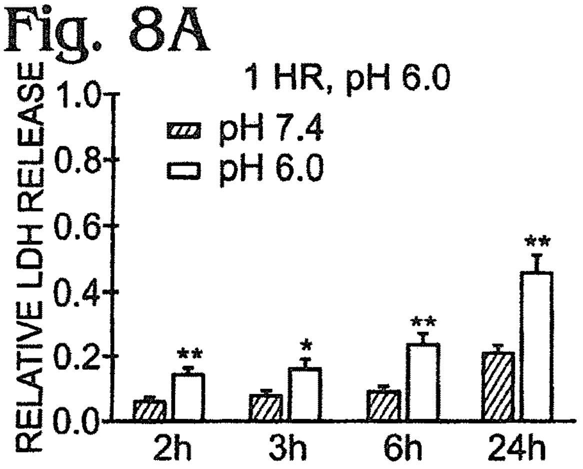
FIGS. 8A-8C are a series of graphs presenting exemplary data showing that acid incubation may induce glutamate receptor-independent neuronal injury that is protected by ASIC blockade, in accordance with aspects of the present teachings.
Figure 8B:
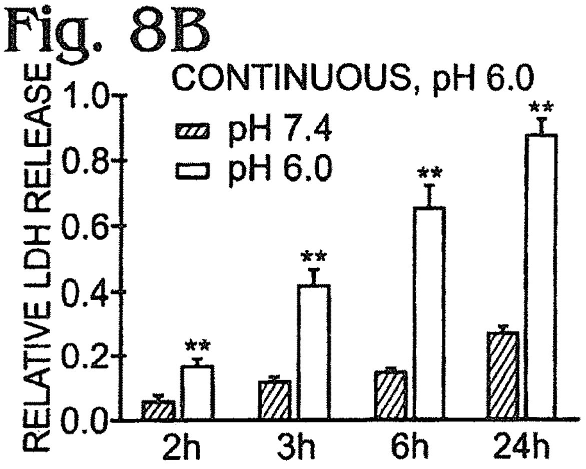

4. ASIC Blockade Protects Acidosis-Induced, Glutamate-Independent Neuronal Injury FIG. 8 shows exemplary data suggesting that acid incubation may induce glutamate receptor-independent neuronal injury protected by ASIC blockade. FIGS. 8A and 8B show graphs presenting exemplary data for time-dependent LDH release induced by 1 hr (FIG. 8A) or 24 hr incubation (FIG. 8B) of cortical neurons in pH 7.4 (solid bars) or 6.0 ECF (open bars). N=20-25 wells, *p<0.05, and p<0.01, compared to pH 7.4 group at the same time points. (Acid-induced neuronal injury with fluorescein diacetate (FDA) also was analyzed by staining of cell bodies of alive neurons and propidium iodide (PI) staining of nuclei of dead neurons.) FIG. 8**C shows a graph illustrating inhibition of acid-induced LDH release by 100 μM amiloride or 100 ng/mL PcTX venom (n=20-27, *p<0.05, and p<0.01). MK801, CNQX, and nimodipine were present in ECF for all experiments (FIGS. 8**A-C).

Acid-induced injury was studied on neurons grown on 24-well plates incubated in either pH 7.4 or 6.0 ECF containing MK801, CNQX, and nimodipine; see FIG. 8. Cell injury was assayed by the measurement of lactate dehydrogenase (LDH) release (Koh and Choi, 1987) at various time points (FIGS. 8A and 8B) and by fluorescent staining of alive/dead cells. Compared to neurons treated at pH 7.4, 1 hr acid incubation (pH 6.0) induced a time-dependent increase in LDH release (FIG. 8A). After 24 hr, 45.7%±5.4% of maximal LDH release was induced (n=25 wells). Continuous treatment at pH 6.0 induced greater cell injury (FIG. 8B, n=20). Consistent with the LDH assay, alive/dead staining with fluorescein diacetate (FDA, blue) and propidium iodide (PI, red) showed similar increases in cell death by 1 hr acid treatment (see Supplemental Figure S3 (on the web site cited above), which is incorporated herein by reference). One hour incubation with pH 6.5 ECF also induced significant but less LDH release than with pH 6.0 ECF (n=8 wells).

Figure 8C:
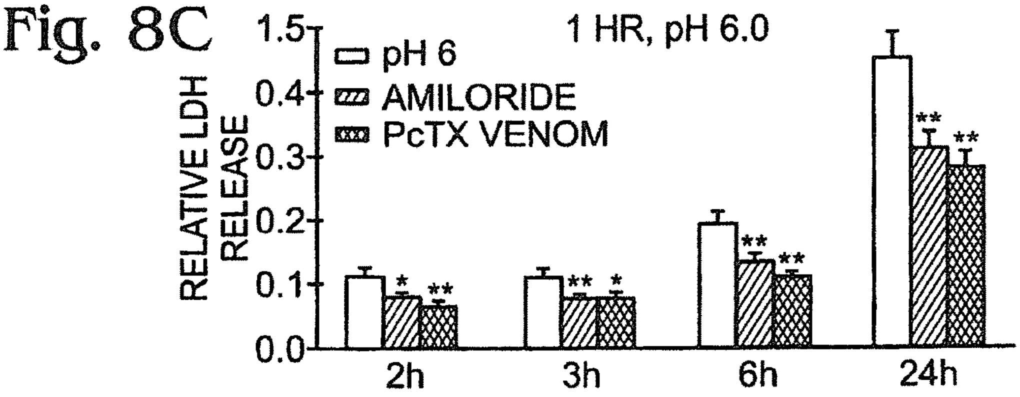

To determine whether activation of ASICs is involved in acid-induced glutamate receptor-independent neuronal injury, we tested the effect of amiloride and PcTX venom on acid-induced LDH release. Addition of either 100 μM amiloride or 100 ng/mL PcTX venom 10 min before and during the 1 hr acid incubation significantly reduced LDH release (FIG. 8C). At 24 hr, LDH release was decreased from 45.3%±3.8% to 31.1%±2.5% by amiloride and to 27.9%±2.6% by PcTX venom (n=20-27, p<0.01). Addition of amiloride or PcTX venom in pH 7.4 ECF for 1 hr did not affect baseline LDH release, although prolonged incubation (e.g., 5 hr) with amiloride alone increased LDH release (n=8).

Figures 9A, 9B, 9C, 9D:
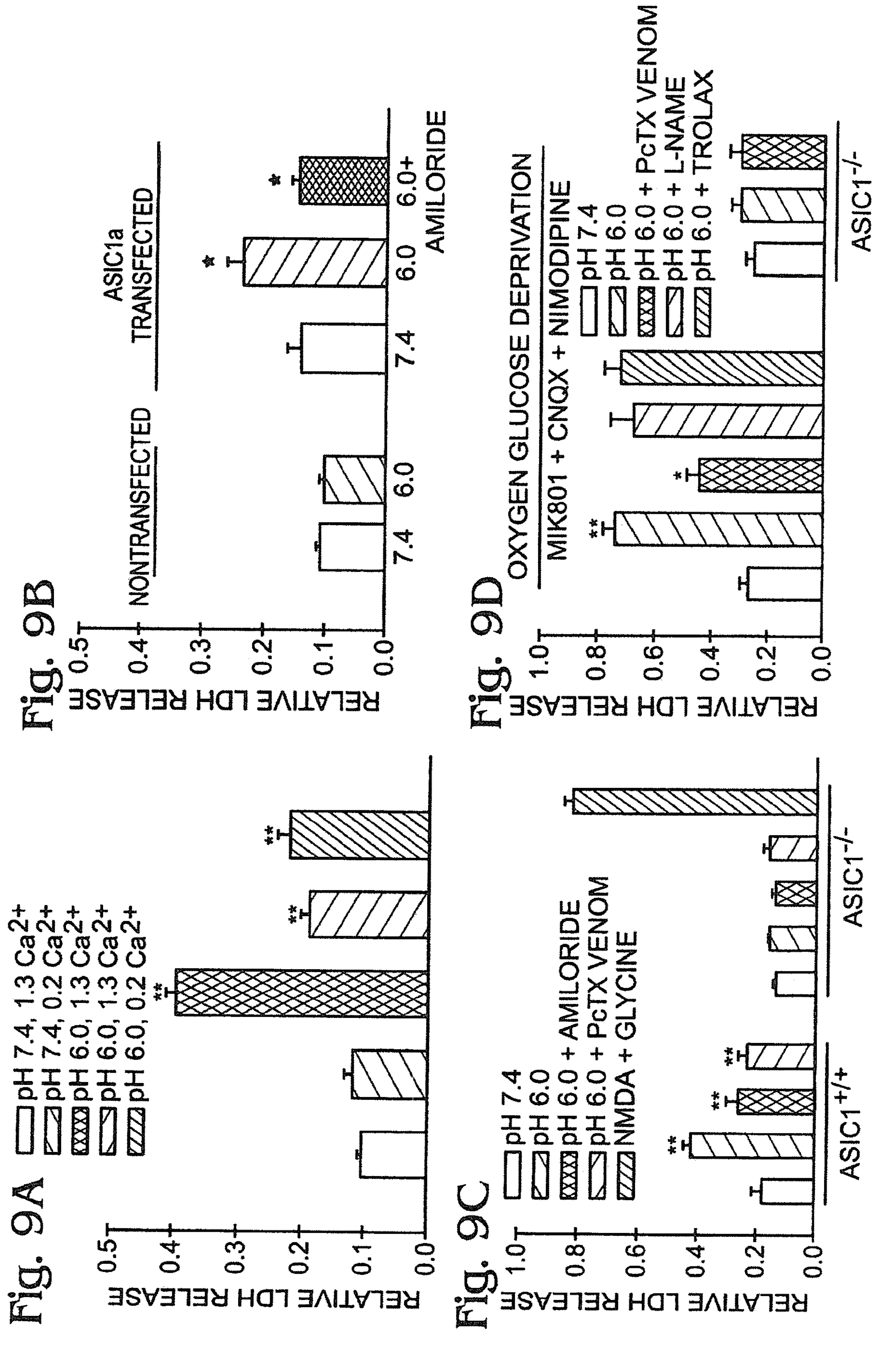
FIGS. 9A-9D are a series of graphs presenting exemplary data showing that ASIC1a may be involved in acid-induced injury in vitro, in accordance with aspects of the present teachings.

5. Activation of Homomeric ASIC1a May be Responsible for Acidosis-Induced Injury FIG. 9 is a series of graphs presenting exemplary data indicating that ASIC1a may be involved in acid-induced injury in vitro. FIG. 9A shows exemplary data illustrating inhibition of acid-induced LDH release by reducing $[Ca^{2+}]_e$ (n=11-12, p<0.01 compared with pH 6.0, 1.3 $Ca^{2+}$). FIG. 9**B shows exemplary data illustrating acid incubation induced increase of LDH release in ASIC1a-transfected but not nontransfected COS-7 cells (n=8-20). Amiloride (100 μM) inhibited acid-induced LDH release in ASIC1a-transfected cells. *p<0.05 for 7.4 versus 6.0 and 6.0 versus 6.0+amiloride. FIG. 9C shows exemplary data illustrating a lack of acid-induced injury and protection by amiloride and PcTX venom in $ASIC1^{-/-}$ neurons (n=8 in each group, p>0.05). FIG. 9D shows exemplary data illustrating acid-induced increase of LDH release in cultured cortical neurons under OGD (n=5). LDH release induced by combined 1 hr OGD/acidosis was not inhibited by trolox and L-NAME (n=8-11). OGD did not potentiate acid-induced LDH release in $ASIC1^{-/-}$ neurons. **p<0.01 for pH 7.4 versus pH 6.0 and *p<0.05 for pH 6.0 versus 6.0+PcTX venom. MK801, CNQX, and nimodipine were present in ECF for all experiments (FIG. 9A-D).

To determine whether $Ca^{2+}$ entry plays a role in acid-induced injury, we treated neurons with pH 6.0 ECF in the presence of normal or reduced $[Ca^{2+}]_e$; see FIG. 9. Reducing $Ca^{2+}$ from 1.3 to 0.2 mM inhibited acid-induced LDH release (from 40.0%±4.1% to 21.9%±2.5%), as did ASIC1a blockade with PcTX venom (n=11-12, p<0.01; FIG. 9A). $Ca^{2+}$-free solution was not tested, as a complete removal of $[Ca^{2+}]_e$ may activate large inward currents through a $Ca^{2+}$-sensing cation channel, which may otherwise complicate data interpretation (Xiong et al., 1997). Inhibition of acid injury by both amiloride and PcTX, nonspecific and specific ASIC1a blockers, and by reducing $[Ca^{2+}]_e$ suggests that activation of $Ca^{2+}$-permeable ASIC1a may be involved in acid-induced neuronal injury.

To provide additional evidence that activation of ASIC1a is involved in acid injury, we studied acid injury of non-transfected and ASIC1a transfected COS-7 cells, a cell line commonly used for expression of ASICs due to its lack of endogenous channels (Chen et al. 1998; Immke and McCleskey 2001 and Escoubas et al. 2000). Following confluence (36-48 hr after plating), cells were treated with either pH 7.4 or 6.0 ECF for 1 hr. LDH release was measured 24 hr after acid incubation. Treatment of nontransfected COS-7 cells with pH 6.0 ECF did not induce increased LDH release when compared with pH 7.4-treated cells (10.3%±0.8% for pH 7.4, and 9.4%±0.7% for pH 6.0, N=19 and 20 wells; p>0.05, FIG. 9B). However, in COS-7 cells stably transfected with ASIC1a, 1 hr incubation at pH 6.0 significantly increased LDH release from 15.5%±2.4% to 24.0%±2.9% (n=8 wells, p<0.05). Addition of amiloride (100 μM) inhibited acid-induced LDH release in these cells (FIG. 9B).

We also studied acid injury of CHO cells transiently transfected with cDNAs encoding GFP alone or GFP plus ASIC1a. After the transfection (24-36 hr), cells were incubated with acidic solution (pH 6.0) for 1 hr, and cell injury was assayed 24 hr following the acid incubation. As shown in Supplemental Figure S4 (at the website cited above), which is incorporated herein by reference, 1 hr acid incubation largely reduced surviving GFP-positive cells in GFP/ASIC1a group but not in the group transfected with GFP alone (n=3 dishes in each group).

To further demonstrate an involvement of ASIC1a in acidosis-induced neuronal injury, we performed cell toxicity experiments on cortical neurons cultured from ASIC and $ASIC1^{-/-}$ mice (Wemmie et al., 2002). Again, 1 hr acid incubation of $ASIC^{+/+}$ neurons at 6.0 induced substantial LDH release that was reduced by amiloride and PcTX venom (n=8-12). One hour acid treatment of $ASIC1^{-/-}$ neurons, however, did not induce significant increase in LDH release at 24 hr (13.8%±0.9% for pH 7.4 and 14.2%±1.3% for pH 6.0, N=8, p>0.05), indicating resistance of these neurons to acid injury (FIG. 9C). In addition, knockout of the ASIC1 gene also eliminated the effect of amiloride and PcTX venom on acid-induced LDH release (FIG. 9C, n=8 each), further suggesting that the inhibition of acid-induced injury of cortical neurons by amiloride and PcTX venom (FIG. 8C) was due to blockade of ASIC1 subunits. In contrast to acid incubation, 1 hr treatment of $ASIC1^{-/-}$ neurons with 1 mM NMDA+10 μM glycine (in $Mg^{2+}$-free [pH 7.4] ECF) induced 84.8%±1.4% of maximal LDH release at 24 hr (n=4, FIG. 9C), indicating normal response to other cell injury processes.

6. Modeled Ischemia Enhances Acidosis-Induced Glutamate-Independent Neuronal Injury Via ASICs As the magnitude of ASIC currents may be potentiated by cellular and neurochemical components of brain ischemia-cell swelling, arachidonic acid, and lactate (Allen and Attwell 2002 and Immke and McCleskey 2001)-and, more importantly, the desensitization of ASIC currents may be reduced dramatically by modeled ischemia (see FIGS. 5A and 5C), we expected that activation of ASICs in ischemic conditions should produce greater neuronal injury. To test this hypothesis, we subjected neurons to 1 hr acid treatment under oxygen and glucose deprivation (OGD). MK801, CNQX, and nimodipine were added to all solutions to inhibit voltage-gated $Ca^{2+}$ channels and glutamate receptor-mediated cell injury associated with OGD (Kaku et al., 1991). One hour incubation with pH 7.4 ECF under OGD conditions induced only 27.1%±3.5% of maximal LDH release at 24 hr (n=5, FIG. 9D). This finding is in agreement with a previous report that 1 hr OGD does not induce substantial cell injury with the blockade of glutamate receptors and voltage-gated $Ca^{2+}$ channels (Aarts et al., 2003). However, 1 hr OGD, combined with acidosis (pH 6.0), induced 73.9%±4.3% of maximal LDH release (n=5, FIG. 9D, p<0.01), significantly larger than acid-induced LDH release in the absence of OGD (see FIG. 8A, p<0.05). Addition of the ASIC1a blocker PcTX venom (100 ng/mL) significantly reduced acid/OGD-induced LDH release to 44.3%±5.3% (n=5, p<0.05, FIG. 9D).

We also performed the same experiment with cultured neurons from the $ASIC1^{-/-}$ mice. Unlike in ASICI containing neurons, however, 1 hr treatment with combined OGD and acid only slightly increased LDH release in $ASIC1^{-/-}$ neurons (from 26.1%±2.7% to 30.4%±3.5%, N=10-12, FIG. 9D). This finding suggests that potentiation of acid-induced injury by OGD may be due largely to OGD potentiation of ASIC1-mediated toxicity.

Aarts et al. (2003) have recently studied ischemia molded by prolonged OGD (2 hr) but without acidosis. In this model system, they demonstrated activation of a $Ca^{2+}$-permeable nonselective cation conductance activated by reactive oxygen/nitrogen species resulting in glutamate receptor-independent neuronal injury. The prolonged OGD-induced cell injury modeled by Aarts et al. may be reduced dramatically by agents either scavenging free radicals directly (e.g., trolox) or reducing the production of free radicals (e.g., L-NAME) (Aarts et al., 2003). To determine whether combined short duration OGD and acidosis induced neuronal injury may involve a similar mechanism, we tested the effect of trolox and L-NAME on OGD/acid-induced LDH release. As shown in FIG. 9D, neither trolox (500 μM) nor L-NAME (300 μM) had significant effect on combined 1 hr OGD/acidosis-induced neuronal injury (n=8-11). Additional experiments demonstrated that the ASIC blockers amiloride and PcTX venom had no effect on the conductance of TRPM7 channels reported to be responsible for prolonged OGD-induced neuronal injury by Aarts et al. (2003) (Supplemental Figure S5 (see website listed above), which is incorporated herein by reference). Together, these findings strongly suggest that activation of ASICs but not TRPM7 channels may be largely responsible for combined 1 hr OGD/acidosis-induced neuronal injury in our studies.

7. Activation of ASIC1a in Ischemic Brain Injury In Vivo

FIG. 10 shows data illustrating neuroprotection by ASICI blockade and ASICI gene knockout in brain ischemia in vivo. FIG. 10A shows a graph of exemplary data obtained from TTC-stained brain sections illustrating the stained volume ("infarct volume") in brains from aCSF (n=7), amiloride (n=11), or PcTX venom (n=5) injected rats. *p<0.05 and p<0.01 compared with aCSF injected group. FIG. 10**B shows a graph of exemplary data illustrating reduction in infarct volume in brains from $ASIC1^{-/-}$ mice (n=6 for each group). *p<0.05 and p<0.01 compared with +/+ group. FIG. 10C shows a graph of exemplary data illustrating reduction in infarct volume in brains from mice i.p. injected with 10 mg/kg memantine (Mem) or i.p. injection of memantine accompanied by i.c.v. injection of PcTX venom (500 ng/mL). p<0.01 compared with aCSF injection and between memantine and memantine plus PcTX venom (n=5 in each group). FIG. 10D shows a graph of exemplary data illustrating reduction in infarct volume in brains from either $ASIC1^{+/+}$ (wt) or $ASIC1^{-/-}$ mice i.p. injected with memantine (n=5 in each group). *p<0.05, and **p<0.01.

Figure 10A:
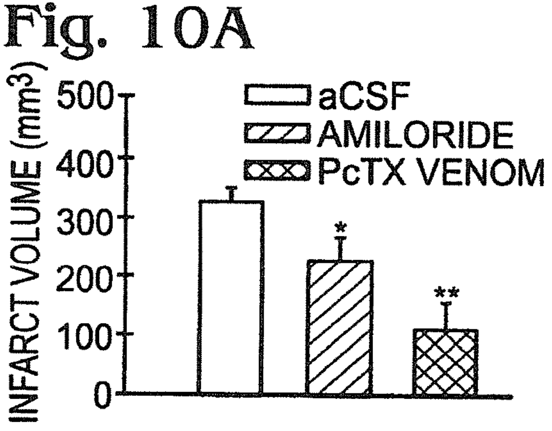
FIGS. 10A-10D are a series of graphs with data showing neuroprotection in brain ischemia in vivo by ASIC1a blockade and by ASIC1 gene knockout, in accordance with aspects of the present teachings.

To provide evidence that activation of ASIC1a may be involved in ischemic brain injury in vivo, we first tested the protective effect of amiloride and PcTX venom in a rat model of transient focal ischemia (Longa et al., 1989). Ischemia (100 min) was induced by transient middle cerebral artery occlusion (MCAO). A total of 6 .μl artificial CSF (aCSF) alone, aCSF-containing amiloride (1 mM), or PcTX venom (500 ng/mL) was injected intracerebroventricularly 30 min before and after the ischemia. Based on the study by Westergaard (1969), the volume for cerebral ventricular and spinal cord fluid for 4-week-old rats is estimated to be ~60 μl. Assuming that the infused amiloride and PcTX were uniformly distributed in the CSF, we may expect a concentration of ~100 μM for amiloride and ~50 ng/mL for PcTX, which is a concentration found effective in our cell culture experiments. Infarct volume was determined by TTC staining (Bederson et al., 1986) at 24 hr following ischemia. Ischemia (100 min) produced an infarct volume of 329.5±25.6 $mm^3$ in aCSF-injected rats (n=7) but only 229.7±41.1 $mm^3$ in amiloride-injected (n=11, p<0.05) and 130.4±55.0 $mm^3$ (~60% reduction) in PcTX venom-injected rats (n=5, p<0.01) (FIG. 10A).

Figure 10B:
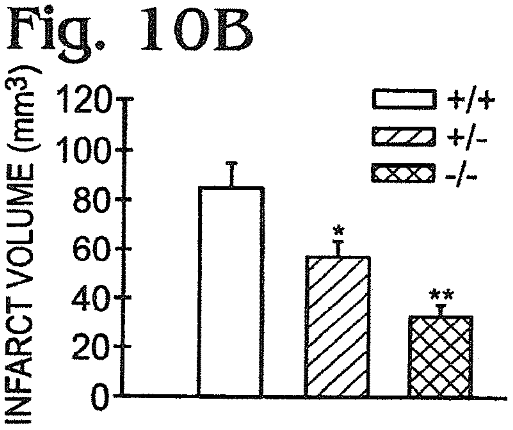

We next used $ASIC1^{-/-}$ mice to further demonstrate the involvement of ASIC1a in ischemic brain injury in vivo. Male $ASIC1^{+/+}$, $ASIC1^{+/-}$, and $ASIC1^{-/-}$ mice (~25 g, with congenic C57B16 background) were subjected to 60 min MCAO as previously described (Stenzel-Poore et al., 2003). Consistent with the protection by pharmacological blockade of ASIC1a (above), −/− mice displayed significantly smaller (~61% reduction) infarct volumes (32.9±4.7 $mm^3$, N=6) as compared to +/+ mice (84.6±10.6 $mm^3$, N=6, p<0.01). +/− mice also showed reduced infarct volume (56.9.+−0.6.7 $mm^3$, N=6, p<0.05) (FIG. 10B).

Figure 10C:
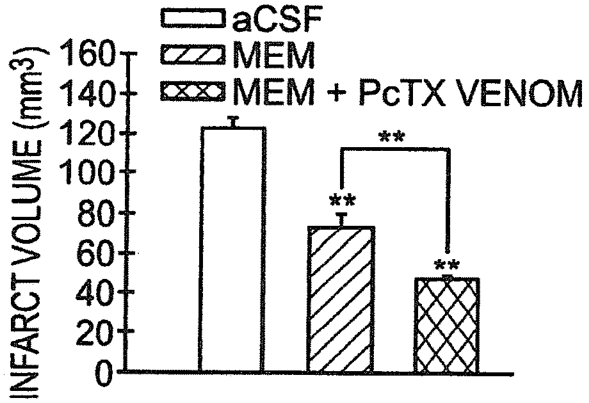
Figure 10D:
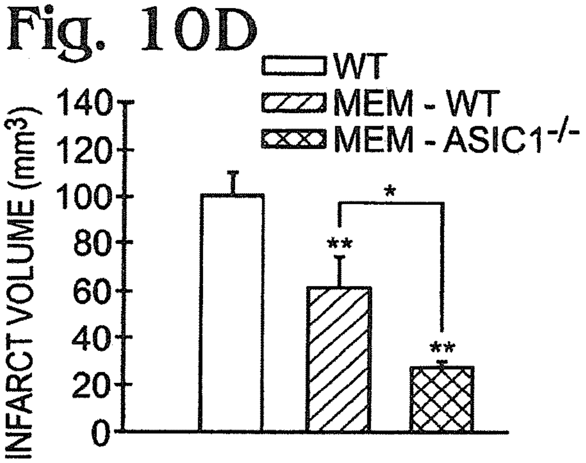

We then determined whether blockade of ASIC1a channels or knockout of the ASIC1 gene could provide additional protection in vivo in the setting of glutamate receptor blockade. We selected the uncompetitive NMDA receptor antagonist memantine, as it has been recently used in successful clinical trials (Tariot et al., 2004). Memantine (10 mg/kg) was injected intraperitoneally (i.p.) into C57B16 mice immediately following 60 min MCAO and accompanied by intracerebroventricular injection (i.c.v.) of a total volume of 0.4 μl aCSF alone or aCSF containing PcTX venom (500 ng/mL) 15 min before and following ischemia. In control mice with i.p. injection of saline and i.c.v.

injection of aCSF, 60 min MCAO induced an infarct volume of 123.6±5.3 $mm^3$ (n=5, FIG. 10C). In mice with i.p. injection of memantine and i.c.v. injection of aCSF, the same duration of ischemia induced an infarct volume of 73.8.+−0.6.9 $mm^3$ (n=5, p<0.01). However, in mice injected with memantine and PcTX venom, an infarct volume of only 47.0±1.1 $mm^3$ was induced (n=5, p<0.01 compared with both control and memantine groups, FIG. 10C). These data suggest that blockade of homomeric ASIC1a may provide additional protection in in vivo ischemia in the setting of NMDA receptor blockade. Additional protection was also observed in $ASIC1^{-/-}$ mice treated with pharmacologic NMDA blockade (FIG. 10D). In $ASIC^{+/+}$ mice i.p. injected with saline or 10 mg/kg memantine, 60 min MCAO induced an infarct volume of 101.4±9.4 $mm^3$ or 61.6±12.7 $mm^3$, respectively (n=5 in each group, FIG. 10D). However, in $ASIC1^{-/-}$ mice injected with memantine, the same ischemia duration induced an infarct volume of 27.7±1.6 $mm^3$ (n=5), significantly smaller than the infarct volume in $ASIC1^{+/+}$ mice injected with memantine (p<0.05).

D. Discussion

Despite enormous recent progress defining cellular and molecular responses of the brain to ischemia, there is no effective treatment for stroke patients. Most notable are the failures of multicenter clinical trials of glutamate antagonists (Lee et al. 1999 and Wahlgren and Ahmed 2004). Here we demonstrate a new mechanism of ischemic brain injury and the role of ischemic acidosis in this biology. We show that ischemic injury in the setting of acidosis may occur via activation of $Ca^{2+}$-permeable ASICs, a newly described class of ligand-gated channels (Waldmann et al., 1997a, and Waldmann and Lazdunski, 1998). This $Ca^{2+}$ toxicity may be independent of glutamate receptors or voltage-gated $Ca^{2+}$ channels.

Using whole-cell patch-clamp recording in mixed cortical cultures, we demonstrate activation of ASIC currents in the range of $pH_e$ (extracellular pH) that occurs commonly in ischemia. With Fura-2 fluorescent imaging and ion substitution protocols, we show ASICs may flux $Ca^{2+}$ in cortical neurons and may do so in the presence of NMDA, AMPA, and voltage-gated $Ca^{2+}$ channel blockade. Using in vitro cell toxicity models, we demonstrate that acidosis may induce glutamate-independent neuronal injury, which may be reduced by both nonspecific and specific ASIC1a antagonists, and by lowering $[Ca^{2+}]_e$. In addition, we show that neurons and COS-7 cells lacking ASIC1a may be resistant to acid injury, while transfection of COS-7 cells with $Ca^{2+}$-permeable ASIC1a may result in acid sensitivity. Using in vivo focal ischemia models, we demonstrate that pharmacologic blockade of ASIC1a channels and ASIC1a gene knockout may both protect the brain from ischemic injury and may do so in the presence of NMDA blockade.

Local $[H^+]$ may be the agonist for ASICs functioning during normal synaptic transmission in the brain (Wemmie et al., 2002). This signaling may not be injurious. However, ASICs also may respond to the global, marked pH declines that may be occurring in the ischemic brain. Within 1 min of global ischemia, $pH_e$ falls from 7.2 to 6.5 (Simon et al., 1985), a level that may be sufficient to activate ASIC1a channels, which have a $pH_{0.5}$ at 6.2. Remarkably, ischemia itself, modeled in vitro, markedly may enhance the magnitude of ASIC response at a given level of acidosis, thus potentiating toxic $Ca^{2+}$ loading in ischemic neurons. Furthermore, ischemia dramatically may reduce desensitization of ASIC currents, signifying a possibility of long-lasting activity of ASICs during prolonged ischemic acidosis in vivo.

It has been shown in intact animals that brief global reductions of brain pH to 6.5 alone do not produce brain injury (Litt et al., 1985), nor does hypoxia alone (Miyamoto and Auer, 2000, and Pearigen et al., 1996). However, our in vitro data suggest that the combination of ischemia (hypoxia) with acidosis (ischemic acidosis), as may occur in vivo, may cause marked brain injury through ischemia enhancing the toxic effect of ASIC1a channels. This argument is strongly supported by the finding that both ASIC1a blockade and ASIC1a gene knockout produce substantial (~60%) reduction in infarct volume.

Acidosis, apart from affecting ischemic brain injury via ASICs, may affect the function of other channels as well. Particularly pertinent in ischemia may be the acid blockade of the NMDA channels (Tang et al. 1990 and Traynelis and Cull-Candy 1990), which may be protective against in vitro ischemic neuronal injury (Kaku et al. 1993 and Giffard et al. 1990). This NMDA blockade in the ischemic brain by acidosis might in part explain the failure of NMDA antagonists in human stroke trials. Treatment of stroke with ASIC1a blockade may be particularly effective, as ischemic acidosis may be serving as an additional therapy by blocking NMDA function.

As our in vitro studies showing a protective effect of ASIC1a blockade were performed in the presence of antagonists of NMDA, AMPA, and voltage-gated $Ca^{2+}$ channels, the findings reported here may offer a new and robust neuroprotective strategy for stroke, either alone or in combination with other therapies (MacGregor et al., 2003). Further, we demonstrate in vivo that pharmacologic ASIC1a blockade or ASIC1a gene deletion may offer more potent neuroprotection against stroke than NMDA antagonism.

Together, our studies suggest that activation of $Ca^{2+}$-permeable ASIC1a may be a novel, glutamate-independent biological mechanism underlying ischemic brain injury. As the regulation of other potentially protective ASIC subunits also occurs in the ischemic brain (Johnson et al., 2001), these findings may help the design of novel therapeutic neuroprotective strategies for brain ischemia.

E. Experimental Procedures

1. Neuronal Culture

Following anesthesia with halothane, cerebral cortices were dissected from E16 Swiss mice or P1 $ASIC1^{+/+}$ and $ASIC1^{-/-}$ mice and incubated with 0.05% trypsin-EDTA for 10 min at 37° C. Tissues were then triturated with fire-polished glass pipettes and plated on poly-L-ornithine-coated 24-well plates or 25×25 mm glass coverslips at a density of $2.5\times10^5$ cells per well or $10^{6+}$ cells per coverslip. Neurons were cultured with MEM supplemented with 10% horse serum (for E16 cultures) or Neurobasal medium supplemented with B27 (for P1 cultures) and used for electrophysiology and toxicity studies after 12 days. Glial growth was suppressed by addition of 5-fluoro-2-deoxyuridine and uridine, yielding cultured cells with 90% neurons as determined by NeuN and GFAP staining (data not shown).

2. Electrophysiology

ASIC currents were recorded with whole-cell patch-clamp and fast-perfusion techniques. The normal extracellular solution (ECF) contained (in mM) 140 NaCl, 5.4 KCl, 25 HEPES, 20 glucose, 1.3 $CaCl_2$, 1.0 $MgCl_2$, 0.0005 TTX (pH 7.4), 320-335 mOsm. For low pH solutions, various amounts of HCl were added. For solutions with pH<6.0, MES instead of HEPES was used for more reliable pH buffering. Patch electrodes contained (in mM) 140 CsF, 2.0 $MgCl_2$, 1.0 $CaC_2$, 10 HEPES, 11 EGTA, 4 MgATP (pH 7.3), 300 mOsm. The $Na^+$-free solution consisted of 10 mM $CaCl_2$, 25 mM HEPES with equiosmotic NMDG or sucrose substituting for NaCl (Chu et al., 2002). A multibarrel perfusion system (SF-77B, Warner Instrument Co.) was employed for rapid exchange of solutions.

3. Cell Injury Assay—LDH Measurement

Cells were washed three times with ECF and randomly divided into treatment groups. MK801 (10 μM), CNQX (20 μM), and nimodipine (5 μM) were added in all groups to eliminate potential secondary activation of glutamate receptors and voltage-gated $Ca^{2+}$ channels. Following acid incubation, neurons were washed and incubated in Neurobasal medium at 37° C. LDH release was measured in culture medium using the LDH assay kit (Roche Molecular Biochemicals). Medium (100 μL) was transferred from culture wells to 96-well plates and mixed with 100 μL reaction solution provided by the kit. Optical density was measured at 492 nm 30 min later, utilizing a microplate reader (Spectra Max Plus, Molecular Devices). Background absorbance at 620 was subtracted. The maximal releasable LDH was obtained in each well by 15 min incubation with 1% Triton X-100 at the end of each experiment.

4. $Ca^{2+}$ Imaging

Cortical neurons grown on 25×25 mm glass coverslips were washed three times with ECF and incubated with 5 μM fura-2-acetoxymethyl ester for 40 min at 22° C., washed three times, and incubated in normal ECF for 30 min. Coverslips were transferred to a perfusion chamber on an inverted microscope (Nikon TE300). Cells were illuminated using a xenon lamp and observed with a 40× UV fluor oil-immersion objective lens, and video images were obtained using a cooled CCD camera (Sensys KAF 1401, Photometrics). Digitized images were acquired and analyzed in a PC controlled by Axon Imaging Workbench software (Axon Instruments). The shutter and filter wheel (Lambda 10-2) were controlled by the software to allow timed illumination of cells at 340 or 380 nm excitation wavelengths. Fura-2 fluorescence was detected at emission wavelength of 510 nm. Ratio images (340/380) were analyzed by averaging pixel ratio values in circumscribed regions of cells in the field of view. The values were exported to SigmaPlot for further analysis.

5. Fluorescein-Diacetate Staining and Propidium Iodide Uptake

Cells were incubated in ECF containing fluorescein-diacetate (FDA) (5 μM) and propidium iodide (PI) (2 μM) for 30 min followed by wash with dye-free ECF. Alive (FDA-positive) and dead (PI-positive) cells were viewed and counted on a microscope (Zeiss) equipped with epifluorescence at 580/630 nm excitation/emission for PI and 500/550 nm for FDA. Images were collected using an Optronics DEI-730 camera equipped with a BQ 8000 sVGA frame grabber and analyzed using computer software (Bioquant, Tenn.).

6. Transfection of COS-7 Cells

COS-7 cells were cultured in MEM with 10% HS and 1% PenStrep (GIBCO). At ~50% confluence, cells were cotransfected with cDNAs for ASICs and GFP in $pc^{DNA3}$ vector using FuGENE6 transfection reagents (Roche Molecular Biochemicals). DNA for ASICs (0.75 μg) and 0.25 μg of DNA for GFP were used for each 35 mm dish. GFP-positive cells were selected for patch-clamp recording 48 hr after transfection. For stable transfection of ASIC1a, 500 μg/mL G418 was added to culture medium I week following the transfection. The surviving G418-resistant cells were further plated and passed for >5 passages in the presence of G418. Cells were then checked with patch-clamp and immunofluorescent staining for the expression of ASIC1a.

7. Oxygen-Glucose Deprivation

Neurons were washed three times and incubated with glucose-free ECF at pH 7.4 or 6.0 in an anaerobic chamber (Model 1025, Forma Scientific) with an atmosphere of 85% $N_2$, 10% $H_2$, and 5% $CO_2$ at 35° C. Oxygen-glucose deprivation (OGD) was terminated after 1 hr by replacing the glucose-free ECF with Neurobasal medium and incubating the cultures in a normal cell culture incubator. With HEPES-buffered ECF used, 1 hr OGD slightly reduced pH from 7.38 to 7.28 (n=3) and from 6.0 to 5.96 (n=4).

8. Focal Ischemia

Transient focal ischemia was induced by suture occlusion of the middle cerebral artery (MCAO) in male rats (SD, 250-300 g) and mice (with congenic C57B16 background, ~25 g) anesthetized using 1.5% isoflurane, 70% $N_{20}$, and 28.5% $O_2$ with intubation and ventilation. Rectal and temporalis muscle temperature was maintained at 37° C.±0.5° C. with a thermostatically controlled heating pad and lamp. Cerebral blood flow was monitored by transcranical LASER doppler. Animals with blood flow not reduced below 20% were excluded.

Animals were killed with chloral hydrate 24 hr after ischemia. Brains were rapidly removed, sectioned coronally at 1 mm (mice) or 2 mm (rats) intervals, and stained by immersion in vital dye (2%) 2,3,5-triphenyltetrazolium hydrochloride (TTC). Infarction area was calculated by subtracting the normal area stained with TTC in the ischemic hemisphere from the area of the nonischemic hemisphere. Infarct volume was calculated by summing infarction areas of all sections and multiplying by slice thickness. Rat intraventricular injection was performed by stereotaxic technique using a microsyringe pump with cannula inserted stereotactically at 0.8 mm posterior to bregma, 1.5 mm lateral to midline, and 3.8 mm ventral to the dura. All manipulations and analyses were performed by individuals blinded to treatment groups.

REFERENCES

Aarts, M., Iihara, K., Wei, W. L., Xiong, Z. G., Arundine, M., Cerwinski, W., MacDonald, J. F. and Tymianski, M., 2003. A key role for TRPM7 channels in anoxic neuronal death. Cell 115, pp. 863-877.

Akopian, A. N., Chen, C. C., Ding, Y., Cesare, P. and Wood, J. N., 2000. A new member of the acid-sensing ion channel family. Neuroreport 11, pp. 2217-2222.

Allen, N. J. and Attwell, D., 2002. Modulation of ASIC channels in rat cerebellar Purkinje neurons by ischemia-related signals. J. Physiol. 543, pp. 521-529.

Alvarez de la Rosa, D., Zhang, P., Shao, D., White, F. and Canessa, C. M., 2002. Functional implications of the localization and activity of acid-sensitive channels in rat peripheral nervous system. Proc. Natl. Acad. Sci. USA 99, pp. 2326-2331.

Alvarez de la Rosa, D., Krueger, S. R., Kolar, A., Shao, D., Fitzsimonds, R. M. and Canessa, C. M., 2003. Distribution, subcellular localization and ontogeny of ASIC1 in the mammalian central nervous system. J. Physiol. 546, pp. 77-87.

Bassilana, F., Champigny, G., Waldmann, R., De Weille, J. R., Heurteaux, C. and Lazdunski, M., 1997. The acid-sensitive ionic channel subunit ASIC and the mammalian degenerin MDEG form a heteromultimeric H+-gated Na+ channel with novel properties. J. Biol. Chem. 272, pp. 28819-28822.

Bederson, J. B., Pitts, L. H., Germano, S. M., Nishimura, M. C., Davis, R. L. and Bartkowski, H. M., 1986. Evaluation of 2,3,5-triphenyltetrazolium chloride as a stain for detection and quantification of experimental cerebral infarction in rats. Stroke 17, pp. 1304-1308.

Benos, D. J. and Stanton, B. A., 1999. Functional domains within the degenerin/epithelial sodium channel (Deg/ENaC) superfamily of ion channels. J. Physiol. 520, pp. 631-644.

Benson, C. J., Eckert, S. P. and McCleskey, E. W., 1999. Acid-evoked currents in cardiac sensory neurons: a possible mediator of myocardial ischemic sensation. Circ. Res. 84, pp. 921-928.

Bevan, S. and Yeats, J., 1991. Protons activate a cation conductance in a sub-population of rat dorsal root ganglion neurones. J. Physiol. 433, pp. 145-161.

Bianchi, L. and Driscoll, M., 2002. Protons at the gate: DEG/ENaC ion channels help us feel and remember. Neuron 34, pp. 337-340.

Chen, C. C., England, S., Akopian, A. N. and Wood, J. N., 1998. A sensory neuron-specific, proton-gated ion channel. Proc. Natl. Acad Sci. USA 95, pp. 10240-10245.

Chen, C. C., Zimmer, A., Sun, W. H., Hall, J., Brownstein, M. J. and Zimmer, A., 2002. A role for ASIC3 in the modulation of high-intensity pain stimuli. Proc. Natl. Acad Sci. USA 99, pp. 8992-8997.

Choi, D. W., 1988. Calcium-mediated neurotoxicity: relationship to specific channel types and role in ischemic damage. Trends Neurosci. 11, pp. 465-469 a.

Choi, D. W., 1988. Glutamate neurotoxicity and diseases of the nervous system. Neuron 1, pp. 623-634 b.

Choi, D. W., 1995. Calcium: still center-stage in hypoxic-ischemic neuronal death. Trends Neurosci. 18, pp. 58-60.

Chu, X. P., Miesch, J., Johnson, M., Root, L., Zhu, X. M., Chen, D., Simon, R. P. and Xiong, Z. G., 2002. Proton-gated channels in PC12 cells. J. Neurophysiol. 87, pp. 2555-2561.

Dingledine, R., Borges, K., Bowie, D. and Traynelis, S. F., 1999. The glutamate receptor ion channels. Pharmacol. Rev. 51, pp. 7-61.

Escoubas, P., De Weille, J. R., Lecoq, A., Diochot, S., Waldmann, R., Champigny, G., Moinier, D., Menez, A. and Lazdunski, M., 2000. Isolation of a tarantula toxin specific for a class of proton-gated Na+ channels. J. Biol. Chem. 275, pp. 25116-25121.

Giffard, R. G., Monyer, H., Christine, C. W. and Choi, D. W., 1990. Acidosis reduces NMDA receptor activation, glutamate neurotoxicity, and oxygen-glucose deprivation neuronal injury in cortical cultures. Brain Res. 506, pp. 339-342.

Goldberg, M. P. and Choi, D. W., 1993. Combined oxygen and glucose deprivation in cortical cell culture: calcium-dependent and calcium-independent mechanisms of neuronal injury. J. Neurosci. 13, pp. 3510-3524.

Grunder, S., Geissler, H. S., Bassler, E. L. and Ruppersberg, J. P., 2000. A new member of acid-sensing ion channels from pituitary gland. Neuroreport 11, pp. 1607-1611.

Immke, D. C. and McCleskey, E. W., 2001. Lactate enhances the acid-sensing Na+ channel on ischemia-sensing neurons. Nat. Neurosci. 4, pp. 869-870.

Jia, Z., Agopyan, N., Miu, P., Xiong, Z., Henderson, J., Gerlai, R., Tavema, F. A., Velumian, A., MacDonald, J., Carlen, P. et al., 1996. Enhanced LTP in mice deficient in the AMPA receptor GluR2. Neuron 17, pp. 945-956.

Johnson, M. B., Jin, K., Minami, M., Chen, D. and Simon, R. P., 2001. Global ischemia induces expression of acid-sensing ion channel 2a in rat brain. J. Cereb. Blood Flow Metab. 21, pp. 734-740.

Kaku, D. A., Goldberg, M. P. and Choi, D. W., 1991. Antagonism of non-NMDA receptors augments the neuroprotective effect of NMDA receptor blockade in cortical cultures subjected to prolonged deprivation of oxygen and glucose. Brain Res. 554, pp. 344-347.

Kaku, D. A., Giffard, R. G. and Choi, D. W., 1993. Neuroprotective effects of glutamate antagonists and extracellular acidity. Science 260, pp. 1516-1518.

Koh, J. Y. and Choi, D. W., 1987. Quantitative determination of glutamate mediated cortical neuronal injury in cell culture by lactate dehydrogenase efflux assay. J. Neurosci. Methods 20, pp. 83-90.

Krishtal, O., 2003. The ASICs: signaling molecules?. Modulators? Trends Neurosci. 26, pp. 477-483.

Krishtal, O. A. and Pidoplichko, V. I., 1981. A receptor for protons in the membrane of sensory neurons may participate in nociception. Neuroscience 6, pp. 2599-2601.

Lee, J. M., Zipfel, G. J. and Choi, D. W., 1999. The changing landscape of ischaemic brain injury mechanisms. Nature Suppl. 399, pp. A7-14.

Lingueglia, E., De Weille, J. R., Bassilana, F., Heurteaux, C., Sakai, H., Waldmann, R. and Lazdunski, M., 1997. A modulatory subunit of acid sensing ion channels in brain and dorsal root ganglion cells. J. Biol. Chem. 272, pp. 29778-29783.

Litt, L., Gonzalez-Mendez, R., Severinghaus, J. W., Hamilton, W. K., Shuleshko, J., Murphy-Boesch, J. and James, T. L., 1985. Cerebral intracellular changes during supercarbia: an in vivo 31P nuclear magnetic resonance study in rats. J. Cereb. Blood Flow Metab. 5, pp. 537-544.

Longa, E. Z., Weinstein, P. R., Carlson, S. and Cummins, R., 1989. Reversible middle cerebral artery occlusion without craniectomy in rats. Stroke 20, pp. 84-91.

MacGregor, D. G., Avshalumov, M. V. and Rice, M. E., 2003. Brain edema induced by in vitro ischemia: causal factors and neuroprotection. J. Neurochem. 85, pp. 1402-1411.

McDonald, J. W., Bhattacharyya, T., Sensi, S. L., Lobner, D., Ying, H. S., Canzoniero, L. M. and Choi, D. W., 1998. Extracellular acidity potentiates AMPA receptor-mediated cortical neuronal death. J. Neurosci. 18, pp. 6290-6299.

McLennan, H., 1983. Receptors for the excitatory amino acids in the mammalian central nervous system. Prog. Neurobiol. 20, pp. 251-271.

Meldrum, B. S., 1995. Excitatory amino acid receptors and their role in epilepsy and cerebral ischemia. Ann. N Y Acad Sci. 757, pp. 492-505.

Miyamoto, O. and Auer, R. N., 2000. Hypoxia, hyperoxia, ischemia, and brain necrosis. Neurology 54, pp. 362-371.

Nedergaard, M., Kraig, R. P., Tanabe, J. and Pulsinelli, W. A., 1991. Dynamics of interstitial and intracellular pH in evolving brain infarct. Am. J. Physiol. 260, pp. R581-R588.

Pearigen, P., Gwinn, R. and Simon, R. P., 1996. The effects in vivo of hypoxia on brain injury. Brain Res. 725, pp. 184-191.

Price, M. P., Snyder, P. M. and Welsh, M. J., 1996. Cloning and expression of a novel human brain Na+ channel. J. Biol. Chem. 271, pp. 7879-7882.

Price, M. P., Lewin, G. R., Mcllwrath, S. L., Cheng, C., Xie, J., Heppenstall, P. A., Stucky, C. L., Mannsfeldt, A. G., Brennan, T. J., Drummond, H. A. et al., 2000. The mammalian sodium channel BNC1 is required for normal touch sensation. Nature 407, pp. 1007-1011.

Price, M. P., Mcllwrath, S. L., Xie, J., Cheng, C., Qiao, J., Tarr, D. E., Sluka, K. A., Brennan, T. J., Lewin, G. R. and Welsh, M. J., 2001. The DRASIC cation channel contributes to the detection of cutaneous touch and acid stimuli in mice. Neuron 32, pp. 1071-1083.
Rehncrona, S., 1985. Brain acidosis. Ann. Emerg. Med 14, pp. 770-776.
Rothman, S. M. and Olney, J. W., 1986. Glutamate and the pathophysiology of hypoxic-ischemic brain damage. Ann. Neurol. 19, pp. 105-111.
Sattler, R., Xiong, Z., Lu, W. Y., Hafner, M., MacDonald, J. F. and Tymianski, M., 1999. Specific coupling of NMDA receptor activation to nitric oxide neurotoxicity by PSD-95 protein. Science 284, pp. 1845-1848.
Siesjo, B. K., Katsura, K. and Kristian, T., 1996. Acidosis-related damage. Adv. Neurol. 71, pp. 209-233.
Simon, R. P., Swan, J. H., Griffiths, T. and Meldrum, B. S., 1984. Blockade of N-methyl-D-aspartate receptors may protect against ischemic damage in the brain. Science 226, pp. 850-852.
Simon, R. P., Benowitz, N., Hedlund, R. and Copeland, J., 1985. Influence of the blood-brain pH gradient on brain phenobarbital uptake during status epilepticus. J. Pharmacol. Exp. Ther. 234, pp. 830-835.
Sluka, K. A., Price, M. P., Breese, N. M., Stucky, C. L., Wemmie, J. A. and Welsh, M. J., 2003. Chronic hyperalgesia induced by repeated acid injections in muscle is abolished by the loss of ASIC3, but not ASIC1. Pain 106, pp. 229-239.
Stenzel-Poore, M. P., Stevens, S. L., Xiong, Z., Lessov, N. S., Harrington, C. A., Mori, M., Meller, R., Rosenzweig, H. L., Tobar, E., Shaw, T. E. et al., 2003. Effect of ischaemic preconditioning on genomic response to cerebral ischaemia: similarity to neuroprotective strategies in hibernation and hypoxia-tolerant states. Lancet 362, pp. 1028-1037.
Swanson, R. A., Farrell, K. and Simon, R. P., 1995. Acidosis causes failure of astrocyte glutamate uptake during hypoxia. J. Cereb. Blood Flow Metab. 15, pp. 417-424.
Tang, C. M., Dichter, M. and Morad, M., 1990. Modulation of the N-methyl-D-aspartate channel by extracellular H+. Proc. Natl. Acad. Sci. USA 87, pp. 6445-6449.
Tariot, P. N., Farlow, M. R., Grossberg, G. T., Graham, S. M., McDonald, S. and Gergel, I., 2004. Memantine treatment in patients with moderate to severe Alzheimer disease already receiving donepezil: a randomized controlled trial. JAMA 291, pp. 317-324.
Tombaugh, G. C. and Sapolsky, R. M., 1993. Evolving concepts about the role of acidosis in ischemic neuropathology. J. Neurochem. 61, pp. 793-803.
Traynelis, S. F. and Cull-Candy, S. G., 1990. Proton inhibition of N-methyl-D-aspartate receptors in cerebellar neurons. Nature 345, pp. 347-350.
Ugawa, S., Ueda, T., Ishida, Y., Nishigaki, M., Shibata, Y. and Shimada, S., 2002. Amiloride-blockable acid-sensing ion channels are leading acid sensors expressed in human nociceptors. J. Clin. Invest. 110, pp. 1185-1190.
Varming, T., 1999. Proton-gated ion channels in cultured mouse cortical neurons. Neuropharmacology 38, pp. 1875-1881.
Wahlgren, N. G. and Ahmed, N., 2004. Neuroprotection in cerebral ischaemia: facts and fancies—the need for new approaches. Cerebrovasc. Dis. Supp. 17, pp. 153-166.
Waldmann, R. and Lazdunski, M., 1998. H(+)-gated cation channels: neuronal acid sensors in the NaC/DEG family of ion channels. Curr. Opin. Neurobiol. 8, pp. 418-424.
Waldmann, R., Champigny, G., Bassilana, F., Heurteaux, C. and Lazdunski, M., 1997a. A proton-gated cation channel involved in acid-sensing. Nature 386, pp. 173-177.
Waldmann, R., Bassilana, F., de Weille, J., Champigny, G., Heurteaux, C. and Lazdunski, M., 1997b. Molecular cloning of a non-inactivating proton-gated Na+ channel specific for sensory neurons. J. Biol. Chem. 272, pp. 20975-20978.
Waldmann, R., Champigny, G., Lingueglia, E., De Weille, J., Heurteaux, C. and Lazdunski, M., 1999. H(+)-gated cation channels. Ann. N Y Acad. Sci. 868, pp. 67-76.
Wemmie, J. A., Chen, J., Askwith, C. C., Hruska-Hageman, A. M., Price, M. P., Nolan, B. C., Yoder, P. G., Lamani, E., Hoshi, T., Freeman, J. H. and Welsh, M. J., 2002. The acid-activated ion channel ASIC contributes to synaptic plasticity, learning, and memory. Neuron 34, pp. 463-477.
Wemmie, J. A., Askwith, C. C., Lamani, E., Cassell, M. D., Freeman Jr., J. H. and Welsh, M. J., 2003. Acid-sensing ion channel 1 is localized in brain regions with high synaptic density and contributes to fear conditioning. J. Neurosci. 23, pp. 5496-5502.
Westergaard, E., 1969. The cerebral ventricles of the rat during growth. Acta Anat. (Basel) 74, pp. 405-423.
Xiong, Z., Lu, W. and MacDonald, J. F., 1997. Extracellular calcium sensed by a novel cation channel in hippocampal neurons. Proc. Natl. Acad. Sci. USA 94, pp. 7012-7017.
Yermolaieva, O., Leonard, A. S., Schnizler, M. K., Abboud, F. M. and Welsh, M. J., 2004. Extracellular acidosis increases neuronal cell calcium by activating acid-sensing ion channel 1a. Proc. Natl. Acad. Sci. USA 101, pp. 6752-6757.
Ying, W., Han, S. K., Miller, J. W. and Swanson, R. A., 1999. Acidosis potentiates oxidative neuronal death by multiple mechanisms. J. Neurochem. 73, pp. 1549-1556.

Example 2: Time Window of PcTX Neuroprotection

Figure 11:
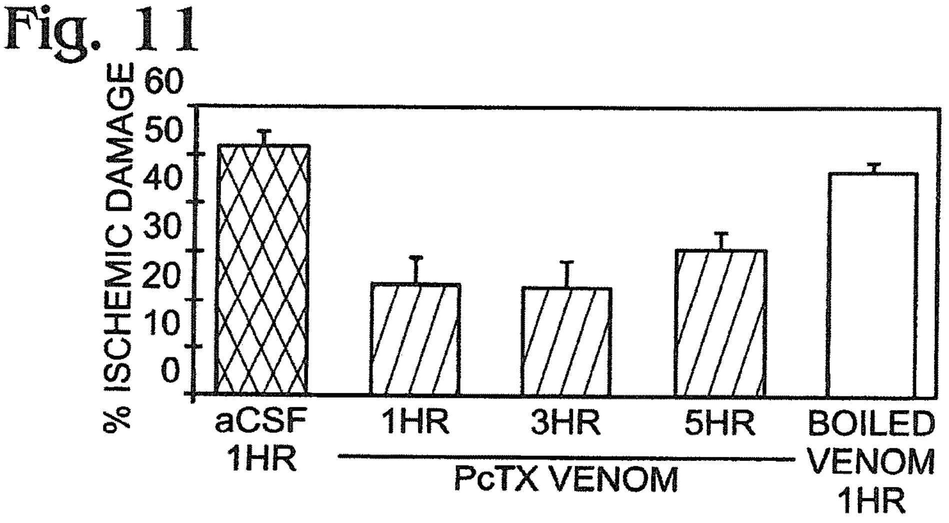
FIG. 11 is a graph plotting exemplary data for the percentage of ischemic damage produced by stroke in an animal model system as a function of the time and type of treatment, in accordance with aspects of the present teachings.

This example describes exemplary experiments that measure the neuroprotective effect of PcTX venom at different times after onset of stroke in rodents; see FIG. 11. Brain ischemia (stroke) was induced in rodents by mid-cerebral artery occlusion (MCAO). At the indicated times after induction, artificial cerebrospinal fluid (aCSF), PcTX venom (0.5 μL, 500 ng/mL total protein), or inactivated (boiled) venom was infused into the lateral ventricles of each rodent. Administration of PcTX venom provided a 60% reduction in stroke volume both at one hour and at three hours after stroke onset. Furthermore, substantial stroke volume reduction still may be maintained if treatment is withheld for five hours after the onset of the MCAO. Accordingly, neuroprotection due to ASIC inhibition may have an extended therapeutic time window after stroke onset, allowing stroke subjects to benefit from treatment performed hours after the stroke began. This effect of ASIC blockade on stroke neuroprotection is far more robust than that of calcium channel blockade of the NMDA receptor (a major target for experimental stroke therapeutics) using a glutamate antagonist. No glutamate antagonist, thus far, has such a favorable profile as shown here for ASIC1a-selective inhibition.

Example 3: Exemplary Cystine Knot Peptides

Figure 12:
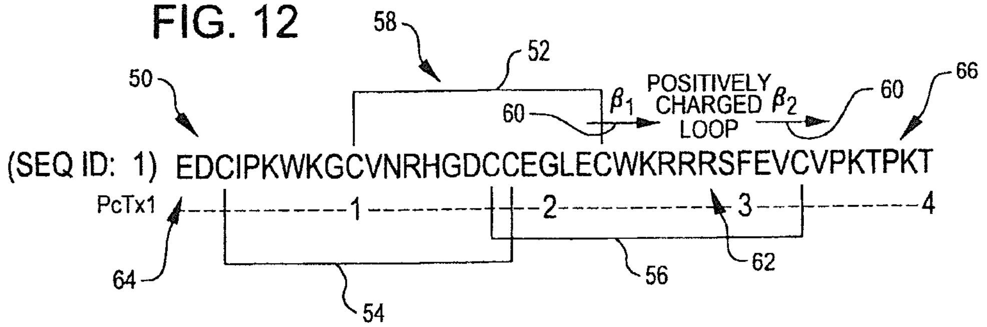
FIG. 12 is a view of the primary amino acid sequence of an exemplary cystine knot peptide, PcTx1, with various exemplary peptide features shown, in accordance with aspects of the present teachings.

This example describes exemplary cystine knot peptides, including full-length PcTx1 and deletion derivatives of PcTx, which may be screened in cultured cells, tested in ischemic animals (e.g., rodents such as mice or rats), and/or administered to ischemic human subjects; see FIGS. 12 and 13.

FIG. 12 shows the primary amino acid sequence (SEQ ID NO:1), in one-letter code, of an exemplary cystine knot peptide, PcTx1, indicated at 50, with various exemplary peptide features shown relative to amino acid positions 1-40. Peptide 50 may include six cysteine residues that form cystine bonds 52, 54, 56 to create a cystine knot motif 58. The peptide also may include one or more beta sheet regions 60 and a positively charged region 62. An N-terminal region 64 and a C-terminal region 66 may flank the cystine knot motif.

FIG. 13 shows a comparison of the PcTx1 peptide 50 of FIG. 12 aligned with various exemplary deletion derivatives of the peptide. These derivatives may include an N-terminal deletion 70 (SEQ ID NO:2), a partial C-terminal deletion 72 (SEQ ID NO:3), a full C-terminal deletion 74 (SEQ ID NO:4), and an N/C terminal deletion 76 (SEQ ID NO:5). Other derivatives of PcTx1 may include any deletion, insertion, or substitution of one or more amino acids, for example, while maintaining sequence similarity or identity of at least about 25% or about 50% with the original PcTx1 sequence.

Each PcTx1 derivative may be tested for its ability to inhibit ASIC proteins selectively and/or for an effect, if any, on ischemia. Any suitable test system(s) may be used to perform this testing including any of the cell-based assay systems and/or animal model systems described elsewhere in the present teachings. The PcTx1 derivative also or alternatively may be tested in ischemic human subjects.

Example 4: Selectivity of PcTX Venom for ASIC1a

This example describes experiments that measure the selectivity of PcTX venom (and thus PcTx1 toxin) for ASIC1a alone, relative to other ASIC proteins or combinations of ASIC proteins expressed in cultured cells; see FIG. 14. COS-7 cells expressing the indicated ASIC proteins were treated with PcTX venom (25 ng/mL on ASIC1a expressing cells and 500 ng/mL on ASIC2a, ASIC3 or ASIC1a+2a expressing cells). Channel currents were measured at the pH of half maximal channel activation (pH 0.5). PcTX venom largely blocked the currents mediated by ASIC1a homomeric channels at a protein concentration of 25 ng/mL, with no effect on the currents mediated by homomeric ASIC2a, ASIC3, or heteromeric ASIC1a/ASIC2a at 500 ng/mL (n=3-6, FIG. 14). At 500 ng/mL, PcTX venom also did not affect the currents mediated by other ligand-gated channels (e.g. NMDA and GABA receptor-gated channels) and voltage-gated channels (e.g. Na+, Ca2+, and K+ channels) (n=4-5). These experiments indicate that PcTX venom and thus PcTx1 peptide is a specific blocker for homomeric ASIC1a. Using this cell-based assay system, the potency and selectivity of ASIC inhibition may be measured for various synthetic peptides or other candidate inhibitors (e.g., see Example 3).

Example 5: Nasal Administration of PcTX Venom is Neuroprotective

This example describes exemplary data indicating the efficacy of nasally administered PcTX venom for reducing ischemia-induced injury in an animal model system of stroke; see FIG. 15. Cerebral ischemia was induced in male mice by mid-cerebral artery occlusion. One hour after occlusion was initiated animals were treated as controls or were treated with PcTX venom (50 μL of 5 ng/mL (total protein) PcTx venom introduced intranasally). Nasal administration of PcTX venom resulted in a 55% reduction in ischemia-induced injury (ischemic damage), as defined by infarct volume, relative to control treatment. Nasal administration may be via a spray that is deposited substantially in the nasal passages rather than inhaled into the lungs and/or may be via an aerosol that is at least partially inhaled into the lungs. In some examples, nasal administration may have a number of advantages over other routes of administration, such as more efficient delivery to the brain and/or adaptability for self-administration by an ischemic subject.

Example 6 Selected Embodiments

This example describes selected embodiments of the present teachings, presented as a series of indexed paragraphs.

1. A method for the treatment of ischemia-induced injury, comprising:

administering a therapeutically effective amount of an inhibitor of an acid sensing ion channel (ASIC) family member to a subject in need thereof.

2. The method of paragraph 1, wherein the step of administering is performed on a stroke patient.

3. The method of paragraph 1, wherein the step of administering is performed based on a risk of the subject for a future ischemic episode or based or due to chronic ischemia.

4. The method of paragraph 1, wherein the step of administering is performed to treat injury induced by ischemic heart disease.

5. The method of paragraph 1, wherein the step of administering includes administering a plurality of doses of the inhibitor to the subject at different times.

6. The method of paragraph 1, wherein the step of administering is performed by injection of the inhibitor.

7. The method of paragraph 1, wherein the step of administering is performed by ingesting or breathing the inhibitor.

8. The method of paragraph 1, wherein the step of administering includes administering an inhibitor of ASIC1 family members.

9. The method of paragraph 8, wherein the step of administering includes administering an inhibitor that is selective for ASIC1 family members relative to other ASIC family members.

10. The method of paragraph 1, wherein the step of administering includes administering an inhibitor of ASIC1a.

11. The method of paragraph 10, wherein the step of administering includes administering an inhibitor that is selective for ASIC1a relative to other ASIC family members.

12. The method of paragraph 11, wherein the step of administering includes administering an inhibitor that is specific for ASIC1 a relative to other ASIC family members.

13. The method of paragraph 1, wherein the step of administering includes administering a peptide having a cystine knot motif.

14. The method of paragraph 13, wherein the step of administering includes administering PcTx1, a toxin peptide from a tarantula species.

15. A method of screening for drugs to treat ischemia-induced injury, comprising:

selecting an assay system for measuring interaction with ASIC1a;

testing a set of compounds for interaction with ASIC1a in the assay system to identify at least one compound that shows interaction;

administering the at least one compound, or a structural relative thereof, to a subject with ischemia to test the efficacy of the at least one compound or the structural relative for treatment of ischemia-induced injury.

16. The method of paragraph 15, wherein the step of selecting an assay system includes selecting an assay system that measures ion flux mediated by ASIC1a.

17. The method of paragraph 16, wherein the step of selecting an assay system includes selecting an assay system that measures flux of calcium mediated by ASIC1a.

18. The method of paragraph 16, wherein the step of testing a set of compounds includes testing the compounds for inhibition of the ion flux.

19. The method of paragraph 15, wherein the step of testing a set of compounds includes a step of testing the set of compounds for selective or specific inhibition of ASIC1a relative to at least one other ASIC family member.

20. A composition for treating ischemia-induced injury, comprising:

an ASIC1a inhibitor configured as a medicament for administration to human subjects.

21. The composition of paragraph 20, wherein the ASIC1a inhibitor is selective or specific for ASIC1a relative to each other ASIC family member.

22. The composition of paragraph 20, wherein the ASIC1a inhibitor is a peptide having a cystine knot motif.

23. The composition of paragraph 22, wherein the peptide is PcTx1, a toxin from a tarantula species.

The disclosure set forth above may encompass one or more distinct inventions, with independent utility. Each of these inventions has been disclosed in its preferred form(s). These preferred forms, including the specific embodiments thereof as disclosed and illustrated herein, are not intended to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure.

What is claimed is:

1. A composition for treatment of ischemia, comprising:

an effective amount of an acid sensing ion channel 1a (ASIC1a) inhibitor comprising a peptide having an amino acid sequence selected from the group consisting of SEQ ID NO:1, SEQ ID NO:2, SEQ ID NO:3, SEQ ID NO:4, and SEQ ID NO:5, and an effective amount of an NMDA receptor inhibitor.

2. The composition of claim 1, wherein the inhibitor of NMDA receptor is a glutamate antagonist.

3. The composition of claim 1, wherein the peptide comprises the amino acid sequence of SEQ ID NO:1.

4. The composition of claim 1, wherein the peptide comprises the amino acid sequence of SEQ ID NO:2.

5. The composition of claim 1, wherein the peptide comprises the amino acid sequence of SEQ ID NO:3.

6. The composition of claim 1, wherein the peptide comprises the amino acid sequence of SEQ ID NO:4.

7. The composition of claim 1, wherein the peptide comprises the amino acid sequence of SEQ ID NO:5.

* * * * *